US008944048B2

(12) United States Patent
Monzyk

(10) Patent No.: US 8,944,048 B2
(45) Date of Patent: Feb. 3, 2015

(54) APPARATUS AND METHODS OF PROVIDING DIATOMIC OXYGEN ($O_2$) USING FERRATE(VI)-CONTAINING COMPOSITIONS

(75) Inventor: Bruce F. Monzyk, Delaware, OH (US)

(73) Assignee: Battelle Memorial Institute, Columbus, OH (US)

( * ) Notice: Subject to any disclaimer, the term of this patent is extended or adjusted under 35 U.S.C. 154(b) by 675 days.

(21) Appl. No.: 12/934,328

(22) PCT Filed: Mar. 26, 2009

(86) PCT No.: PCT/US2009/038472
§ 371 (c)(1),
(2), (4) Date: Sep. 24, 2010

(87) PCT Pub. No.: WO2009/142823
PCT Pub. Date: Nov. 26, 2009

(65) Prior Publication Data
US 2011/0017209 A1    Jan. 27, 2011

Related U.S. Application Data

(60) Provisional application No. 61/039,579, filed on Mar. 26, 2008.

(51) Int. Cl.
| | |
|---|---|
| *A62B 21/00* | (2006.01) |
| *A62B 7/06* | (2006.01) |
| *A61M 16/10* | (2006.01) |
| *C01B 13/02* | (2006.01) |

(52) U.S. Cl.
CPC .............. *A61M 16/10* (2013.01); *A62B 21/00* (2013.01); *C01B 13/0203* (2013.01); *A61M 2202/0208* (2013.01); *A61M 2205/8231* (2013.01)
USPC ................... 128/202.26; 128/200.11; 423/579

(58) Field of Classification Search
USPC .................... 128/202.26, 205.21; 424/43, 44; 423/579, 580.1
See application file for complete search history.

(56) References Cited

U.S. PATENT DOCUMENTS

| | | |
|---|---|---|
| 3,372,125 A | 3/1968 | Hill |
| 3,904,421 A | 9/1975 | Shimizu et al. |
| 4,156,613 A | 5/1979 | Hund |
| 4,225,352 A | 9/1980 | Makino et al. |
| 4,243,494 A | 1/1981 | Riggs, Jr. et al. |

(Continued)

FOREIGN PATENT DOCUMENTS

| | | |
|---|---|---|
| CN | 1524595 | 9/2004 |
| DE | 553004 | 5/1943 |

(Continued)

OTHER PUBLICATIONS

Payerne, "Dr. Payerne's Improved Methods of Supporting Respiration in Concined Places, and of Purifying Mines, Factories, Hospitals, etc." Mechanics Magazine, 1844, No. 1065, p. 1-7.*

(Continued)

*Primary Examiner* — Justine Yu
*Assistant Examiner* — Timothy Stanis
(74) *Attorney, Agent, or Firm* — Yimei C. Hammond; Kremblas & Foster

(57) ABSTRACT

Methods of generating oxygen ($O_2$) are described in which ferrate(VI) is combined with an acid.

7 Claims, 3 Drawing Sheets

(56) References Cited

U.S. PATENT DOCUMENTS

| | | | |
|---|---|---|---|
| 4,256,551 A | 3/1981 | Cliff et al. | |
| 4,606,843 A | 8/1986 | Kaczur | |
| 4,705,726 A | 11/1987 | Shindou et al. | |
| 5,049,306 A * | 9/1991 | Greer | 252/187.31 |
| 5,284,642 A | 2/1994 | Evrard et al. | |
| 5,416,450 A | 5/1995 | Konishi | |
| 5,607,504 A | 3/1997 | Schmid et al. | |
| 5,823,181 A * | 10/1998 | Shih | 128/202.26 |
| 6,080,288 A | 6/2000 | Schwartz et al. | |
| 6,267,896 B1 * | 7/2001 | Patterson et al. | 210/758 |
| 6,471,788 B1 | 10/2002 | Minevski et al. | |
| 6,566,574 B1 | 5/2003 | Tadros et al. | |
| 6,576,346 B1 | 6/2003 | Ravenscroft et al. | |
| 6,723,890 B2 | 4/2004 | Tucker et al. | |
| 6,837,984 B2 | 1/2005 | Wang et al. | |
| 6,899,769 B2 | 5/2005 | Ravenscroft et al. | |
| 6,899,956 B2 | 5/2005 | Block et al. | |
| 7,045,024 B2 | 5/2006 | Minevski et al. | |
| 7,045,051 B2 | 5/2006 | Minevski et al. | |
| 7,291,217 B2 | 11/2007 | Phelps et al. | |
| 7,347,893 B2 | 3/2008 | Low | |
| 7,387,671 B2 | 6/2008 | Meisen et al. | |
| 7,387,672 B2 | 6/2008 | Friedrich | |
| 7,410,536 B2 | 8/2008 | Friedrich et al. | |
| 7,422,793 B2 | 9/2008 | Phelps et al. | |
| 2002/0098989 A1 | 7/2002 | Heimann et al. | |
| 2003/0042134 A1 | 3/2003 | Tremblay et al. | |
| 2003/0055245 A1 | 3/2003 | Tseng et al. | |
| 2003/0146169 A1 | 8/2003 | Ciampi et al. | |
| 2003/0159942 A1 | 8/2003 | Minevski et al. | |
| 2004/0104377 A1 | 6/2004 | Phelps et al. | |
| 2004/0216637 A1 | 11/2004 | Buchheit et al. | |
| 2005/0022810 A1 | 2/2005 | Moore et al. | |
| 2005/0049157 A1 | 3/2005 | MacDonald et al. | |
| 2005/0053543 A1 | 3/2005 | Kneip et al. | |
| 2005/0123743 A1 | 6/2005 | Martinazzo | |
| 2005/0152828 A1 | 7/2005 | Aga et al. | |
| 2006/0134339 A1 | 6/2006 | Wang et al. | |
| 2006/0162613 A1 | 7/2006 | Rosenhahn et al. | |
| 2008/0305341 A1 | 12/2008 | Plieth et al. | |
| 2009/0216060 A1 | 8/2009 | Monzyk et al. | |
| 2011/0017209 A1 | 1/2011 | Monzyk et al. | |

FOREIGN PATENT DOCUMENTS

| | | | |
|---|---|---|---|
| EP | 166825 | | 1/2002 |
| FR | 2805162 | | 8/2001 |
| JP | 59139314 | | 8/1984 |
| JP | 61053398 | | 3/1986 |
| JP | 62007596 | | 1/1987 |
| JP | 62091225 | | 4/1987 |
| JP | 62292492 | | 12/1987 |
| WO | 0121856 | | 3/2001 |
| WO | 0182896 | | 11/2001 |
| WO | WO 0182896 | A1 * | 11/2001 |
| WO | 2005069892 | | 8/2005 |
| WO | 2006015756 | | 2/2006 |
| WO | 2007075153 | | 7/2007 |
| WO | 2008112657 | | 9/2008 |
| WO | 2009142823 | | 11/2009 |
| WO | 2010045657 | | 4/2010 |
| WO | 2012018870 | | 2/2012 |

OTHER PUBLICATIONS

Wood, Robert H, The Heat, Free Energy and Entropy of the Ferrate (VI) Ion, 1958, J. Am. Chem. Soc., 80 (9), pp. 2038-2041.*
Rush, James D, et al., Decay of Ferrate(V) in Neutral and Acidic Solutions. A Premix Pulse Radiolysis Study, 1994, Inorg. Chem., 33, pp. 5499-5502.*
Koch, John C, et al., Chemistry & Chemical Reactivity, 1996, Saunders College Publishing, 3rd Edition, pp. 808, 830-831.*
Sharma, Virender K, Potassium ferrate(VI): an enviornmentally friendly oxidant, 2002, Advances in Environmental Research, 6, pp. 143-156.*
Audette, R.J., Quail, J.W.: "Potassium, Rubidium, Cesium, and Barium Ferrates(VI). Preparations, Infrared Spectra, and Magnetic Susceptibilities". Inorganic Chemistry, [Online], vol. 11, No. 8, Aug. 1972, XP002569971 DOI: 10.1021/ic50114a034 [retrieved on Feb. 23, 2010].
Bouzek, K., Lipovska, M., Schmidt, M., Rousar, I., Wragg, A.A.: "Electrochemical Production of Ferrate(VI) Using Sinusoidal Alternating Current Superimposed on Direct Current: Grey and White Cast Iron Electrodes". Electrochimica Acta, vol. 44 (1998) pp. 547-557.
Bouzek, K., Rousar, I.: "The Study of Electrochemical Preparation of Ferrate(VI) Using Alternating Current Superimposed on the Direct Current Frequency Dependence of Current Yields". Electrochimica Acta, vol. 38, No. 13, 1993, pp. 1717-1720.
Bouzek, K., Flower, L., Rousar, I., Wragg, A.A.: "Electrochemical Production of Ferrate(VI) Using Sinusoidal Alternating Current Superimposed on Direct Current. Pure Iron Electrode". Journal of Applied Electrochemistry, vol. 29, 1999, pp. 569-576.
Bouzek, K., et al. "Influence of Anode Material on Current Yields During Ferrate(VI) Production by Anodic Iron Dissolution Part I: Current Efficiency During Anodic Dissolution of Grey Cast Iron to Ferrate(VI) in Concentrated Alkali Hydroxide Solutions". Journal of Applied Electrochemistry, vol. 26, 1996, pp. 919-923.
Dean, John A. "Lange's Handbook of Chemistry". 15th edition, 1999, McGraw-Hill, New York, 8.104-8.111.
Delaude et al.: "A Novel Oxidizing Reagent Based on Potassium Ferrate(VI)" Journal of Organic Chemistry, vol. 61, 1996, pp. 6360-6370.
Grube, Von G., Gmelin, H.: "Effects of Superimposed Alternating Current on Anode Ferrate Formation". Zeitschrift fur Electrochemie, vol. 26, 1920, pp. 153-161.
He, W., Wang, J., Yang, C., and Zhang, J.: "The Rapid Electrochemical Preparation of Dissolved Ferrate(VI): Effects of Various Operating Parameters". Electrochimica Acta, vol. 51, 2006, pp. 1067-1973.
Hirota, N.: "Anticorrosion Paints". May 12, 1984, XP002569967, database accession No. 1972:476784.
Hives, J., Benova, M., Bouzek, K., Sitek, J., Sharma, V.K.: "The Cyclic Voltammetric Study of Ferrate(VI) Formation in a Molten Na/K hydroxide Mixture". Electrochimica Acta, vol. 54, 2008, pp. 203-208.
Kim, K.S., Chang, Y., Bae, S.K. and Hahn, C.S.: "Selective Oxidation of Allylic and Benzylic Alcohols Using Potassium Ferrate under Phase-Transfer Catalysis Condition". Synthesis, vol. 10, Oct. 1984, pp. 866-868. XP002438865.
Licht, Stuart, Naschitz, Vera, Wang, Baohui: "Rapid Chemical Synthesis of the Barium Ferrate Super-Iron Fe (VI) Compound, BaFeO4". Journal of Power Sources [Online] vol. 109, Jun. 15, 2002, pp. 67-70, XP002569968 DOI: doi:10.1016/S0378-7753 (02)00041-1 [retrieved on Feb. 23, 2010].
Macova, Z., Bouzek, K., Hives, J., Sharma, V.K., Terryn, R.J., Baum, J.C.: "Research Progress in the Electrochemical Synthesis of Ferrate(VI)". Electrochimica Acta, vol. 54, 2009, pp. 2673-2683.
Sharma, Virender K., "Potassium Ferrate(VI): An Environmentally Friendly Oxidant". Advances in Environmental Research 6 (2002) 143-156.
Yang, W., Zhou, Y., Wang, H. and Bi, D.: "Studies on Influence of Various Experimental Conditions on Electrochemical Generation of Ferrate(VI) in NaOH—KOH mixed Electrolyte". Russian Journal of Electrochemistry, vol. 45, No. 7, 2009, pp. 795-799.
First Report mailed May 29, 2009, from Australian Intellectual Property Office, in an Australian patent No. 2005206927.
Notice of Allowance mailed Jun. 4, 2010, from Australian Intellectual Property Office, in an Australian patent No. 2005206927.
The First Office Action from the State Intellectual Property Office of the People's Republic of China mailed on Mar. 10, 2010, in the Chinese patent application No. 200580002471.5.
The Second Office Action from the State Intellectual Property Office of the People's Republic of China mailed on Nov. 4, 2010, in the Chinese patent application No. 200580002471.5.
First Office action mailed on Sep. 10, 2010, in a co-pending US patent application publication No. 20090216060 published on Aug. 27, 2009.

(56) References Cited

OTHER PUBLICATIONS

Second Office action mailed on Jan. 12, 2011, in a co-pending US patent publication No. 20090216060 published on Aug. 27, 2009.
Communication from the European Patent Office mailed on Apr. 11, 2008, in a co-pending European Patent Application No. 05858701.5-1218.
Communication from the European Patent Office mailed on Jun. 18, 2010, in a co-pedning European Patent Appplication No. 05858701.5-1218.
Issuance Notice mailed on Nov. 16, 2010, in a co-pending European Patent Application No. 05858701.5-1218.
Written Opinion of the International Searching Authority for International Application Publication No. WO2007/075153 (Application No. PCT/US2005/04714), published on Jul. 5, 2007.
International Search Report for International Application Publication No. WO2007/075153 (Application No. PCT/US2005/04714), published on Jul. 5, 2007.
Written Opinion of the International Searching Authority for International Application Publication No. WO2008/112657 (Application No. PCT/US2008/056446), published on Sep. 18, 2008.
Written Opinion of the International Searching Authority for International Application Publication No. WO2010/045657 (Application No. PCT/US2009/061204), published on Apr. 22, 2010.
Written Opinion of the International Searching Authority for International Application Publication No. WO2009/142823 (Application No. PCT/US2009/038472), published on Nov. 26, 2009.
Written Opinion of the International Searching Authority for International Application Publication No. WO2005/069892 (Application No. PCT/US2005/001402), published on Aug. 4, 2005.

* cited by examiner

APPARATUS AND METHODS OF PROVIDING DIATOMIC OXYGEN ($O_2$) USING FERRATE(VI)-CONTAINING COMPOSITIONS

RELATED APPLICATION

This application claims priority to U.S. Provisional Patent Application Ser. No. 61/039,579 filed Mar. 26, 2008.

INTRODUCTION

There are many situations that require the administration of oxygen ($O_2$) in the field where oxygen tanks may be unavailable, for example in the treatment of heart attack victims, traffic accident victims, or in underground mines. One company, OXYSURE™ Systems, Inc. sells a device that produces oxygen by mixing two white granular powders in a slurry with a liquid. For example, Ross, in U.S. Pat. No. 7,465,428 mentions the use of sodium carbonate or sodium percarbonate as the source for dioxygen.

Other systems for the synthesis of dioxygen have also been described in the patent literature. For example, Davis in U.S. Pat. No. 6,123,069 (incorporated herein by reference) discloses an oxygen delivery system that utilizes the reaction of sodium perborate with water. PCT patent application WO/1986/002063 (which uses sodium percarbonate) and European patent EP0349349 are other examples of oxygen delivery systems. These systems are all based on peroxygen chemistry which uses a catalyst to cause the thermodynamically spontaneous disproportionation reaction well known to peroxides to occur and thereby produces one mole of dioxygen for two moles of peroxygen compound. Unfortunately, numerous catalysts exist for this disproportionation reaction, including trace metal ions, dust, heat, and others. This catalytic sensitivity causes peroxygen compounds to slowly convert to non-dioxygen forming products gradually on storage, sometimes slowly over weeks and other times quickly, within seconds to hours. Hence, although peroxygen compounds can be used to produce dioxygen compounds they are not practical in this role since they loose strength over time and since emergency first responder materials need to predistributed and stored, often for many years, worldwide until use, and then it is required that they be nearly full strength when needed. Peroxygen compounds are white incolor when pure and still are white when fully discharged. Many hundreds of peroxygen compounds have been investigated for shelf life dioxygen and oxidant candidates for first responders, including inorganic, organic and polymer materials, but this search has not been successful.

Therefore, despite extensive research and development, there remains a need for methods of generating $O_2$ from solids that: possess a high density of oxygen, have sufficient shelf life of at least 6 months, have nontoxic reaction products and by-products, have controlled release of gas, and have an indicating function such that a user can determine whether a composition remains active or is expired.

As described in detail in the sections below, the present invention uses ferrate(VI) in methods for making dioxygen. Ferrate(VI), or "ferrate", is a known material that has been suggested for use in numerous applications.

A very early publication entitled "Dr. Payerne's Diving Bell" published in the Mechanics' Magazine dated January 1844, described the use of "ferrate" which, when combined with water, produced oxygen for use in a diving bell. However, it is highly doubtful that the "ferrate" described in the 1844 publication was ferrate(VI) since ferrate(VI) is permanently stable and a dark purple color, essentially a black solid, but Dr. Payerne's material was very unstable when added to alone to water and was a red solid and therefore more likely ferrate(IV) or ferrate(V) which are more reactive with water to form dioxygen.

Ferrate(VI), has been proposed for use commercially for water purification and its use in treating waste water has been discussed in scores of publications. For example, Deininger et al. in U.S. Pat. Nos. 4,983,306 and 5,380,443 has described treating water to remove metal ion contaminants, especially the transuranic elements. In this method, the pH of the water is adjusted to about 6.5 to about 14. Ferrate is especially useful for waste water treatment since it can remove a broad range of contaminants, disinfects many types of pathogens, removes taste and odors, and the iron(III) products coagulate and flocculate impurities and fall from solution, thereby also clarifying and detoxifying water.

Patterson in U.S. Pat. No. 6,521,265 described a method of clotting blood by topically applying a ferrate paste to a wound. In this method, the compound is stored dry and unmixed and is mixed into a paste with the patient's blood or other aqueous media just prior to its application to a wound. Patterson states that the oxygen produced during the reaction substantially reduces the level of bacteria, virus and fungus at the wound. After treatment, the wound remains open unless the ferrate salt is combined with a bandage that has been impregnated or coated with a dry powder of one of the ferrate salt compositions.

Metal surfaces can be oxidized with a ferrate solution to form an oxide layer. Minevski et al. in U.S. Pat. No. 7,045,024 describe a process in which an aluminum surface is cleaned and then treated with a ferrate solution for a time ranging from about 1 second to about 5 minutes.

Champi et al. in U.S. Pat. No. 6,974,562 and U.S. Published Patent Application No. 2005/0271575 Aldescribe methods of making ferrate immediately prior to use. This is advantageous since ferrate can degrade quickly in the presence of moisture. Champi et al. suggest that the ferrate could be encapsulated for future use in a membrane of molecular sieves, clay, porcelain, or other porous material that is not susceptible to oxidation. The membrane could be slightly water soluble so that the ferrate could be released over time. Champi et al. propose numerous uses for the ferrate, including: as an oxidant to prepare polymer and metal surfaces; removal of color from industrial electrolytic baths, synthesis of Fischer-Tropsch catalysts, purifying hemicellulose, as a selective oxidant in organic chemistry, disinfection as a biocide or virocide, phosphorylase inactivator, paint additive, denitration of flue gas, battery cathode electrodes, detoxifying cyanide from waste water, in cigarette filters, as an oxidant of pulp waste, removal of hydrogen sulfide, purifying waste water and drinking water, as a disinfectant, removal of slime films such as in power plants and shipboard cooling systems, delignification of agricultural residues, removal of textile dyes from wastewater, treatment of boiler chemical cleaning wastes, oxidizing sulfur and cyanide containing compounds generated by oil refineries and coke processing plants, removing Mn from drinking water, removing As from drinking water, destroying chemical warfare agents, removing organic matter from drinking water, purifying water in a Jacuzzi or swimming pool and filtering away the resulting iron precipitates, cleaning waste water from animal and vegetable processing, treatment of any aqueous stream containing biosolids, radioactive cleanup, oxidizing pretreatment of chromium containing films, removing heavy metals from solution, cleaning or disinfecting metallic surfaces in medical devices or in the semi-conductor industry, disinfecting and cleaning instruments and surfaces for medical uses, and cleaning bilge water from ships.

SUMMARY OF THE INVENTION

The invention provides compositions, apparatus, and methods that generate gaseous oxygen from ferrate(VI). Ferrate(VI) is sometimes termed herein as simply "ferrate." Hence "ferrate" is used in this specification to represent ferrate(VI), and the use of oxidation state Roman numerals is also sometimes used to insure unambiguous naming of compounds. Contrary to common use, as used herein, "ferrate" does not refer to just any compound that contains iron when present in anion; for example hexacyanoferrate(II) is not "ferrate" in the descriptions herein.

Peroxides are currently used as emergency oxygen supply for their readily decomposable nature. However, peroxides have short and erratic shelf lives and poor thermal stability. The appearance of powder or liquid peroxide looks the same when it's active or at zero strength—a white powder or colorless solution respectively.

In contrast, the purple powder (or solution) of "ferrate" is an excellent source of diatomic oxygen, $O_2$, or just "oxygen gas" in this document, and is thermally stable for readiness for "on demand" reliable $O_2$ production. The purple powder gradually turns rusty-brown when the oxygen gas is discharged, thus providing a visual indication of the available reactivity strength for $O_2$ production. This inherent color change also enables routine inspection of supplies by first responders during non-emergency inspections and thereby allow any replacement of degraded supplies as a matter or routine maintenance. Ferrate powder can be a drop-in replacement to the available emergency oxygen product, such as OXYSURE™, and have better shelf life and tolerance to storage conditions and handling. Special unique packaging or formulations containing ferrate for diatomic oxygen generation can also be prepared. Ferrate-based oxygen can be used in a variety of applications, including: ambulances, in-home breathing air use, military applications for wounded warfighters, victims of chemical warfare agent attack, driving high velocity projectiles, controlling $pO_2$ values in oxidative and facultative oxidative fermentation processes, during launch emergencies; coal miner rescue, oxygen skin treatments, welding, generating and/or supplementing breathing air in confined spaces (such as aircraft, spacecraft, submersible vehicles, spelunking, scuba diving), and the like.

In one aspect, the invention provides a method of quickly supplying oxygen to a human or nonhuman animal, comprising: generating oxygen by combining ferrate with water in the presence of an acid; and generating a stream of gaseous oxygen comprising at least 0.1 mol of diatomic oxygen ($O_2$) or at least 2 liters of diatomic oxygen (measured at 1 atm, and 20° C.).

In another aspect, the invention provides a method of supplying emergency oxygen, comprising: providing a first composition comprising ferrate; providing a second composition comprising an acid; combining the first and second compositions; providing water with the combination of the first and second compositions; and generating a stream of gaseous oxygen comprising at least 0.1 mol of diatomic oxygen ($O_2$) or at least 2 liters of diatomic oxygen.

In the description of the invention, "providing" includes obtaining a pre-made ferrate-containing composition, or mixing two or more components to make a ferrate-containing composition. The term "comprising" is an open term that means "including," and any of the inventive aspects that are described as "comprising," may, in alternative embodiments be described using the narrower terms "consisting essentially of" or "consisting of." In reference to solid compositions, "%" indicates weight % unless indicated otherwise; for gaseous compositions, "%" indicates molar percent (which is the same as volume percent under standard conditions).

The inventive methods can be further characterized by any of the details provided in the detailed description. Also, either of the above methods further characterized by one or more of the following: generating at least 0.5 mol, or 1 mol, or 10 mol $O_2$; generating at least 0.1 liter diatomic oxygen each minute for 3 minutes, 10 minutes, or 60 minutes; or generating at least 0.2 liter diatomic oxygen each minute for 3 minutes, 10 minutes, or 60 minutes; or generating at least one liter diatomic oxygen each minute for 3 minutes, 10 minutes, or 60 minutes.

In another aspect, the invention provides respiratory apparatus comprising a mixing compartment and a face mask or oral insert or nasal insert wherein the oxygen is generated in the mixing compartment, and the stream passes through the mask or insert where it can be inhaled by the wearer of the device. In some embodiments, the generated oxygen stream is at least 40 volume % oxygen, preferably at least 60 volume %, and in some embodiments at least 90 volume % oxygen. In some preferred embodiments, humid oxygen is generated in the mixing compartment which is more compatible with breathing by avoiding drying of the throat.

In another aspect, the invention provides an oxygen dispenser, comprising: a first compartment comprising ferrate; a second compartment comprising acid; and respiratory apparatus.

In a further aspect, the invention provides a ferrate(VI)-containing composition, comprising: a ferrate(VI)-containing solid; and a solid acid. This composition is further characterized by possessing a reactivity such that, when the composition is mixed with water in a water:ferrate(VI) molar ratio of 5, the resulting aqueous composition has a pH of 8 or less and generates at least 0.1 mole of $O_2$ per mole of ferrate (VI) in the ferrate(VI)-containing composition. In preferred embodiments, the pH and $O_2$ generated are measured 1 minute after mixing, and in some embodiments, 10 minutes after mixing. In some preferred embodiments, the composition is a mixture of ferrate(VI)-containing particles and solid acid particles. A "solid acid" is a solid that, when mixed with water, can function as a protic acid or can generate a protic acid.

This invention includes: methods of using ferrate to supply diatomic or gaseous oxygen, $O_2$, compositions of matter of ferrate formulations (any of the formulations described herein), and ferrate-containing devices.

In preferred embodiments of any of the inventive aspects, ferrate(VI) generates at least 0.1 mol $O_2$ per mol of ferrate (VI), more preferably at least 0.25 mol $O_2$ per mol of ferrate (VI), more preferably at least 0.5 mol $O_2$ per mol of ferrate (VI), and in some embodiments, between 0.2 and 0.75 mol $O_2$ per mol of ferrate(VI). Also, in some preferred embodiments of any of the inventive aspects, ferrate(VI) and acid are combined in a ratio of mol acid:mol ferrate of between 0.5 and 5, in some embodiments 0.5 and 3, and in some embodiments, 1.0 to 2.

DETAILED DESCRIPTION OF THE INVENTION

Figure 1:
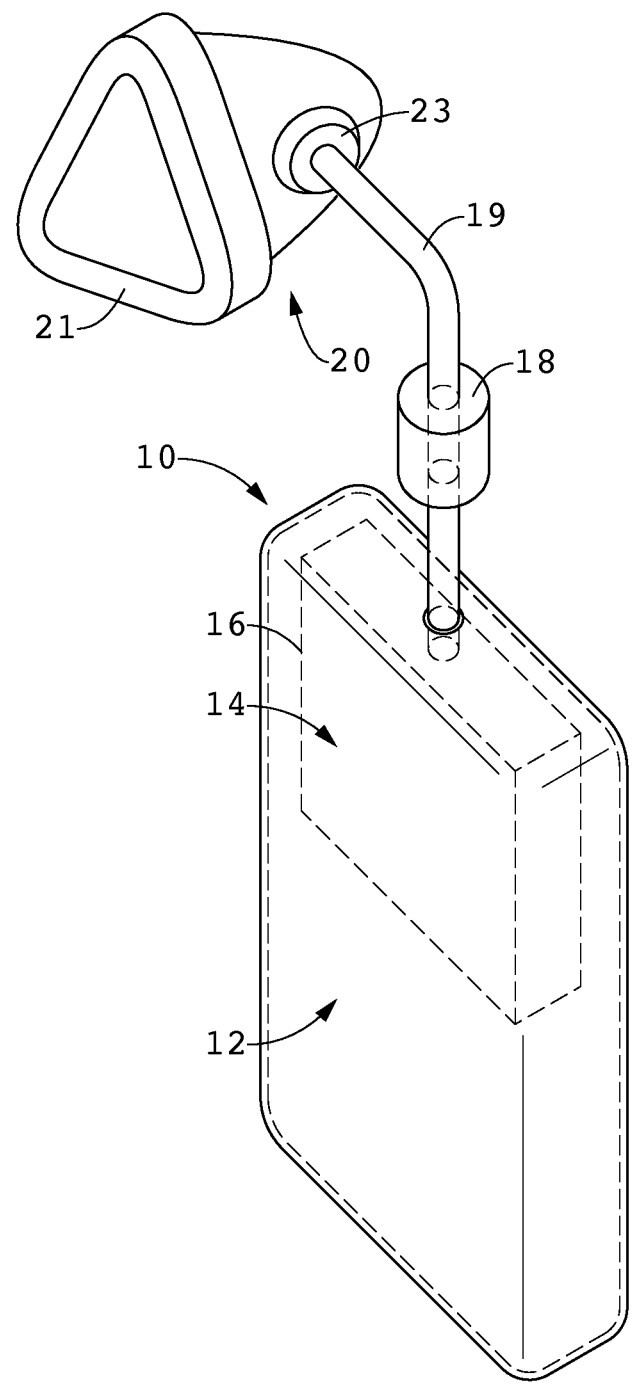
FIG. 1 is a simplified schematic drawing of breathing apparatus.

In the invention, ferrate can be presented as an aqueous solution, slurry, or more preferably a powder, pellet, flake, tablet, lozenge, briquette, as granules, and/or other solid form; for example, comprised of alkali (Na, K, Li, Cs, Rb) and/or alkaline earth (Mg, Ca, Sr, Ba), or zinc ferrate(VI), or alkaline aluminum ferrate(VI) [more preferably selected from sodium ferrate(VI), $Na_2FeO_4$ (shown anhydrous), or most preferably potassium ferrate(VI), $K_2FeO_4$], that would be dissolved at least partially with water and/or an aqueous solution, most preferably an acidic aqueous solution, to accomplish $O_2$ production. Optionally a means of mechanical mixing, including stiffing, ultrasonics, shaking, rocking, and/or the like, can also be provided. Acid type and amount is also critical to achieving the dioxygen generation rates in some preferred embodiments of the invention.

For a single-solid formulation a solid acid can be used. In this event the solid acid ion exchange resins may be used. The dioxygen forming reaction would occur upon mixing with moisture present, or when water is added. The moisture content and/or added water needs to be sufficient to kick off the reaction by dissolving at least a part of the ferrate salt, preferably dissolving at least 5% of the ferrate salt, and most preferably dissolving at least 20% of the ferrate, while dissolving only 1% of the ferrate salt can still be effective in some embodiments of the invention. Then the dissolved ferrate would react with the weak acid ion exchange resin, in $H^+$ form $(RCOOH)_n$, where "n" implies oligomeric or polymeric linear, branched and/or crosslinked poly carboxylic acid molecular structure, or preferably with the strong acid form, such as poly sulfonic acid designated similarly as $(RSO_3H)_n$, where "n" implies oligomeric or polymeric linear, branched and/or crosslinked molecular sulfonic acid structure. Phosphonic acid ion exchange resins are most preferred due to their high acid content per mole, mild pH impact, and tendency to bind up the product ferric ion produced from the ferrate and thereby facilitating removal, handling and disposal. Such resins can carry variable acid content, for example by copolymerization with nonacidic monomers or partial neutralization, and can be aromatic or aliphatically based, and can be porous macroreticular and/or gel structures. Suitable solid beads or granules of commercially available ion exchange resins are preferred and normally contain a water content of at least 20% (by weight), and are typically about 50% moisture.

Ferrate(VI), or just "ferrate" is known by us and published literature as being non-persistent with respect to being hazardous, toxic, or having adverse environmental impact. It is capable of desirable $O_2$ generating chemistry, and is storage and temperature stable. It is also black to purple in color depending on the wt % ferrate(VI) contained therein, even when formulated, and it changes to orange-brown when in spent form (converted to harmless and stable rust like ferric compounds or white phosphate compounds as described above).

In its broader aspects, the invention is not limited to a specific form of ferrate(VI). The chemical form of the ferrate (VI) can be varied, and may be, for example, an essentially pure water soluble salt, an essentially partially water soluble salt, an essentially insoluble water soluble salt, as solid solutions with ions such as with sulfate, oxide, fluoride, orthophosphate, silicate, carbonate, bicarbonate, polyphosphate, pyrophosphate, tripolyphosphate, hydroxide ion, and the like. Such salts of Ferrate(VI) can contain oxidatively resistant or oxidatively inert counter ions (cations) of K, Na, Rb, Cs, Ca, Mg, Zn, Al, Li, La, Ba, Ga, Sr, other lanthanides, Sc, Y, alkyl, aryl, and/or alkylaryl quaternary ammonium ion, a blend of alkyl, aryl, and/or alkylaryl quaternary ammonium ions, including especially those where the amine is resident in a aliphatic or aromatic ring structure, and or where the carbon number of the amine is 18 or greater, as these amines are most oxidatively resistant, alkyl, aryl, and/or alkylaryl phosphonium ion, a blend of phosphonium ions, 1-hexadecylpyridinium ion, N-methyl trialkylammonium ion, N-methyl trialkylbenzene ammonium ion, alone or as solutions, blends, and/or mixtures. Where R— alkyl, aryl, or alkylaryl and/or where substituents such as halogens, nitriles, other phosphonates, carboxylate, nitro groups, pseudo halogens, ether, ester, and/or ketone groups and the like can be included as part of the alkyl or aryl groups such that they do not interfere with the $O_2$ production reaction or are rapidly oxidized by ferrate. Of this list, for aqueous or hydrophilic applications. K, Na, Ca, Mg, Zn, Sr, and Al salts of ferrate or are more preferred, while K and Na is most preferred. For non-aqueous or hydrophobic applications or for hydrophilic/hydrophobic mixtures, inclusion of a quaternary ammonium ion into the operation or product formulation is preferred, and for very hydrophobic conditions, more preferred are quaternary ammonium compounds with total carbon number, CN#, of 4 to 34, and still more preferred are quaternary ammonium compounds with total carbon number of 18 to 34.

In some embodiments, the ferrate(VI) salt comprises of alkali (Na, K, Li, Cs, Rb) and/or alkaline earth (Mg, Ca, Sr, Ba), or zinc ferrate(VI), or alkaline aluminum ferrate(VI) (more preferably selected from sodium ferrate(VI), $Na_2FeO_4$, or most preferably potassium ferrate(VI), $K_2FeO_4$) or any combination of these.

When quaternary ammonium and/or phosphonium compounds are used it is not necessary for this (these) ion(s) to be the ferrate(VI) counter ion as formulated from raw materials. Anionic counter ions of the ammonium, phosphonium or arsonium cations can be other anions including hydroxide ion, carbonate ion, bicarbonate ion, orthophosphate ion, other phosphate ions, including polyphosphates, phosphonate ions, phosphinic ions, fluoride, chloride ion, silicate, borates, carboxylate, sulfonate, sulfate, or other oxidation resistant anions or any blend or combination of these, or the like. We note that most of these anions are also pH buffers and can be used simultaneously to provide such pH buffering to the reaction mixture to control the rate of $O_2$ generation and the final pH of the product "spent" mixture to enable its easy disposal as a nonhazardous solid, slurry, and/or solution.

The amount of ferrate and acid used in a formulation of the invention can vary to control the amount of $O_2$ produced, the size and weight of the apparatus, the cost of the device, the rate of $O_2$ generation, and the like. In some embodiments, ferrate(VI) content (including the mass of cations in the ferrate compound(s)) present in a solid form is present in an at least about 1% by weight of the formulation in some embodiments, about 1 to 10% in others, and in some embodiments from about 10% to about 30% in others, and preferably about 30 to 100%. In some embodiments, a composition contains at least 40%, or at least 50%, or at least 70%, or at least 90%, and in some embodiments is essentially pure ferrate, normally 90-99+%. These amounts can be used to describe a formulation prior to mixing with a second composition to produce oxygen; alternately these amounts can be used to describe a mixed composition prior to the bulk of reaction. Controlling ferrate(VI) content in this manner enables formulation adjustments to match the amount and rate of $O_2$ produced to be matched to the need, and to apparatus size, cost and weight. It also allows the formulation to control the specific reactions conditions and composition of the end product(s).

The emergency applications mentioned for the invention places constraints on the amount of acid and water that can be used to practice the invention since weight, size and portability are important for such devices. Speed of $O_2$ generation and simplicity of use are also important constraints on the viability of a technology efficaciously supplying emergency O2. Ferrate, the oxidant source for $O_2$ generation is a dense material with a formula weight of 198 g/mole and oxidizer equivalent weight of ⅓ this or 66 g/equivalent (for the $K_2FeO_4$ salt), 55.3 g/equivalent (for the $Na_2FeO_4$ salt), or 40 g/equivalent (for the $FeO_4$ ion alone), (since ferrate(VI) absorbs three electrons during a oxidation/reduction reaction). Water is light weight and with its very small equivalent weight as a reductant (9.0 g/equivalent), is sufficient in small amounts to provide sufficient reductant for $O_2$ generation from its reaction with ferrate ion. Hence, at least 9×3 or 27 g of water are required to fully utilize the $O_2$ generation capacity of 40 g of contained ferrate ion ($FeO_4^=$). In practice, since the water is the solvent too, at least twice this ratio of water is preferred, and three times this amount is more preferred, while 5 times this amount is most preferred. However, only ⅕ of this water/ferrate(VI) is still effective in producing $O_2$ gas.

The weight and volume of the oxidatively stable acid used in the invention should be sufficient to maintain the pH of the mixture or solution neutral or slightly acidic. Basic solutions are undesirable since the generation of $O_2$ from ferrate(VI) are slow under basic conditions. However, most acids are not effective in generating $O_2$ efficiently. The acid needs to be oxidatively stable. However, many oxidatively stable inorganic acids are also gases or significantly volatile, such as nitric acid, hydrofluoric acid, hydrochloric acid, and the like. Such volatile gases would contaminate the $O_2$ product and render it unusable in breathing applications if present even in very small amounts. Hence extensive cleanup of the $O_2$ product gas, for example by using a soda lime other basic sorbent, would be required. Likewise, many organic acids also have a significant vapor pressure and smell rank, for example putricine (C5 linear monocarboxcylic acid) and acetic acid are such examples. All monocarboxylic acids of carbon number less than 12 are undesirable. Also, some low equivalent weight carboxylic acids are powerful reducing agents, such has oxalic acid (a diacid) or glycolic acid (a alpha-hydroxy acid) or maleic acid (an unsaturated or olefinic acid), all react faster to be oxidized by ferrate to produce oxidized carbon products, even carbonate or bicarbonate ("mineralization" reactions), and do not form $O_2$ gas even when excess water is provided. Therefore only a select group of acids have been found to be suitable for quickly and weight efficiently generating $O_2$ gas by driving the oxidation reaction between ferrate (VI) and water while not significantly contaminating the $O_2$ produced with acid, oxidized products, or problem fumes while not being also significantly oxidized.

The concentration of ferrate(VI) in a sample can be determined by UV/vis spectrophotometry by comparing the concentrations of ferrate(VI) determined by dissolving in an aqueous solution of 32% NaOH, filtering if necessary (see below) and measuring the absorbance readings at 505 and 785 nm. For the measurement to be qualitatively and quantitatively correct, the concentrations derived from each absorbance reading should be the same within 2-10%. If these two values differ more than 10%, then the spectrum is consistent with ferrate(VI) ion not being the lone chromophore and that another colored or light scattering material is also present. The presence of colloids or particulates is indicated that scatter light causing a false high in the concentration measurement. In this event, further purification of the analytical sample is required, by centrifugation or filtration, to remove these particulates and/or colloids and the absorbance is then re-read at the two diagnostic wavelengths and the acquired UV/vis spectrum in the 400-850 nm wavelength range is inspected as to the proper appearance for the ferrate(VI) ion. In addition, for accurate measurement, care should be taken to avoid conditions that would change the oxidation state of iron. The NaOH solution should be free of reducing agents, preferably by pretreating with ferrate(VI) and filtering. If necessary, where a ferrate(VI) containing composition is strongly hydrophobic, the hydrophobic matrix may be removed (such as with toluene), for example by water washing the ferrate(VI) ion from the hydrophobic phase, just prior to dissolving the ferrate(VI) in 32% NaOH. In instances where the remeasured absorbance's are found to decrease over a period of minutes, then multiple readings are taken at known times and these data are extrapolated back to the time of mixing with the 32% NaOH solution.

Unlike all peroxide materials, we found that potassium ferrate(VI), when produced using the Battelle Process (see published PCT patent application WO2005/069892 by Monzyk et al.) to be thermally stable to storage for long periods, at least 98 days at 71° C., and at least 82 days under conditions of cycling daily from 23° C. to 71° C. and back again. This result is true regardless of whether the potassium ferrate(VI) is pure (80-100% analytical grade) or of only moderate purity (50-80% technical grade). In these tests, losses with time varied slightly with test vials ranging from <1% to 10% (±3%) loss respectively after the test periods given. From these results, it can be estimated that the potassium ferrate(VI) will likely be sufficiently stable for several years of storage, at least. We have stored dried laboratory samples in capped vials for more than five years without significant decomposition.

Despite the strong oxidation potential of ferrate(VI), some useful ferrate(VI) compositions can be made with an oxidation resistant or nonoxidizable matrix materials selected from one or a combination of the following materials: water-polymer, water-oil emulsions, polymer only, oligomer only, water-hydrocarbon, oil only, hydrocarbons only, silicones of all types, alkaline or neutral silicates, silicas including meta silicates, phosphates, phosphate esters, meta phosphates, polyphosphates, phosphonates, borates, boric acid, boric acid esters, fluborates, and carbonates, alone or in combination, and/or with a matrix material in which at least one salt of ferrate(VI) is insoluble or poorly soluble, for example with aliphatic and/or aromatic hydrocarbons such as waxes, petroleum, petroleum jellies, or synthetic oils, creams, ointments, solids, solvents, greases, heat transfer fluids, solvent cleaners, paint thinners, petroleum and/or biodiesel fuels, petroleum jellies, gels, hydraulic fluids, alone or in any combination. Hydrophilic matricides, for example alcohols, polyvinyl alcohols, polyesters, polyethers, ketones, and the like are effective provided the water content is kept less than 10%, and preferably less than 2%, and most preferably less than 0.2%, until the point of need to generate the $O_2$.

A particularly preferred formulation is a combination of ferrate(VI) salt, most preferably the potassium salt and/or sodium salt, with one or more slow or nonoxidizable material(s) and/or one or more matrix materials, with a water content of <10% and preferably <3%, and most preferably <0.3%, in which at least one salt of ferrate(VI), most preferably potassium and/or sodium ferrate(VI) salts, is not soluble. For example, slow or nonoxidizable materials include toluene, benzene, petroleum jelly, and the like, or low moisture polyvinyl alcohol or other polyolefinic alcohol with a water content of <10%, preferably <3%, and most preferably <0.3%.

Hydrophobic materials that are resistant to reaction with ferrate(VI) are desirable matrix materials for some applications. Examples include polyolefins such as polyethylene, polypropylene, polyethers, polyesters, salts of polycarboxylic acids, and the like, alone or in combination as co-polymers or physically blended. The hydrophobic material listed above could be removed, such as by dissolution by an organic solvent, by breaking/grinding of encapsulating costing, and the like prior to use of the ferrate. The use of hydrophilic polymers do not require co-removal, or prior removal of matrix polymer provided the water content of the formulation is kept below 10%, preferably <3%, and most preferably <0.3%, at least until point of desired generation of $O_2$.

To generate oxygen, acids with apparent or actual pKa values less than 9.5, and more preferably less than 7, and most preferably less than 5 are used. Readily oxidized alcohols, amines, aldehydes, thiols, mercaptans, alpha hydroxy ketones, catecholates, and phenolics should be avoided when water is present since $O_2$ will not be produced in a significant extent or not at all due to the faster oxidation of these compounds by the ferrate(VI) rather than the oxidation of water. Protic inorganic acids such as mineral acids, including their protonated basic forms, and acidic metal ion salts such as those containing ferric ion, non basic aluminum ion, titanium (IV) ion, zirconate(IV) ion, copper(II) ion, and the like, and other metal ions that impart an acid pH to water typically should be avoided for use in one part formulations unless they are used in solid form, although they can be used as the acid donor moiety in two or more part formulations. For example concentrated solutions of ferric chloride, ferric sulfate, aluminum sulfate, aluminum chloride, zinc sulfate, zinc chloride, potassium hydrogen fluoride, aluminum bisulfate, zirconium hydrogen phosphate, and the like and mixtures thereof are effective acids used alone or in any combination.

It is not desirable to include any reducible cations or easily dry-state-oxidized functional groups to be used directly with ferrate(VI). If included, such materials should first be rendered oxidation resistant by neutralization of any acidity, derivatization, and/or removal of moisture. Such incompatible materials may be useful where two or more part formulations are stored separately. It is not recommended to combine ferrate(VI) salts with hygroscopic, inorganic solid salts such as KOH, NaOH, $CaCl_2$, and the like since water sorption will initiate $O_2$ production prematurely. However, mixing a ferrate solid with these materials at the point of $O_2$ use is effective and thereby avoids having to carry along or find a source of water. It appears also that it is stabilized if treated with basic salts of phosphate, silicate ion, calcite, and/or potassium sulfate, and combinations thereof. Most preferred are blends of ferrate salts with other components that do not dissolve potassium ferrate(VI) and are not affected by moisture, and preferably those materials that do not dissolve potassium ferrate(VI) but have some affinity for moisture. In this manner any moisture exposure of such ferrate mixtures result in the moisture being held by the non-ferrate materials rather than causing carbonic acid to form from the atmosphere and dissolving the ferrate salt, which would allow the ferrate(VI) to oxidize the moisture to $O_2$ and result in a shorter storage shelf life.

Useful combinations can be prepared, with synergistic effects, include: For example, Part A can be potassium ferrate(VI) salt, optionally with an unreactive component such as potassium sulfate as inert diluent (as a blend or solid solution), physical property modifier (for optimization of particle size, slow release), and stabilizer (for stabilization enhancement), while Part B contains a proton or hydrogen ion donor (for example a pH buffer, an acid (selected as described below from one or a blend of a weak or strong acid, mineral or organic acid, and these alone or in any combination, optionally with water or a component that releases moisture, and/or Part C could contain the water, as a liquid or releasable from a solid, or provision to provide water absorption from the environmental humidity, and be added or would be available (for example absorbed from moist air), optionally this absorption being enhanced by a hygroscopic component (for example KOH or an alkali or alkaline earth and oxidatively resistant salt). Water could be provided, for example, by emission from a deliquescent material, local tap water, a natural water source, deionized water, distilled water, or softened water.

Components from Parts A and B could be in separate packages or containers, or, if very dry, co-mingled as a mixture of particles in one container. Upon blending these Parts of the formulation the ferrate(VI) from Part A becomes mobilized (to the extent of at least 0.1% and more preferably at least about 1%, and most preferably at least about 10% dissolved within a 120 seconds, more preferably within 60 seconds, and most preferably within 20 seconds, with minimal or no added agitation) when contacted with Part B whereupon, as a first step in $O_2$ generation, a solution of the purple $FeO_4^=$ ion is formed by dissolution and the pH of this solution rises, typically resulting in a solution or mixture that it would last for at least one hour, or many hours if more dilute, with only a slow release of $O_2$ gas. The acidity from the acid and/or pH buffer, or other proton or hydrogen ion donor (where "hydrogen ion" includes hydronium ion) from Part B then causes highly reactive intermediate ferrate(VI) ion species to also form. Although we do not wish to be bound by any theories, it is believed that these species are best designated as $HFeO_4^-$ ion for the pH 5 to 8 region, and as $H_2FeO_4$ at still lower pH. These ions or molecules are very reactive due to their very high oxidation potentials and the chemical reactivity provided by protonation which is believed to facilitate opening up the rigid tetrahedral structure of the $FeO_4^=$ ion and facilitating electron transfer, even though the temperature may be cool and the pH mild (e.g. pH 4-10), where these ions and molecules react as oxidants. This high level of reactivity promotes oxidation of the $H_2O$ present and/or the oxide ions bonded to the Fe(VI) ion in $FeO_4^=$ to rapidly form $O_2$ (gas), preferably within 120 seconds, and most preferably within 30 seconds.

Two part formulations between Ferrate(VI) as "Part A" and acidic "Part B" materials where acidic "B" materials (or materials that can be rendered acidic by co-addition of an acid) are oxidatively resistant and can be as one or more parts comprising a combination of one or more of the following materials:

most preferred are one or more oxidatively resistant carboxylic acids of formula R,R',R"CCOOH, where R, R' and/or R" radical groups are bonded to the have at least one C atom that is bonded to the C—COOH moiety, and/or their salts consisting of R,R',R"CCOO— with one or more alkali, alkaline earth, zinc, aluminum, ions alone or in combination, where R, R' and/or R" radical groups are any combination of aromatic and aliphatic groups ("alkylaryl"), of total carbon number range of 1 to about 40 when present as individual compounds, or with a molecular weight of 200 to about 10,000 Daltons when present as oligomers, or with a molecular weight of 2,000 to about 3,000,000 Daltons when present as polymers (including cross-linked aliphatic and/or aromatic polymers), and which can also contain groups or atoms of non-C and H such as halogens, pseudo halogens, oxygen (including ethers, alcohols, carboxylic acids, ketones, aldehydes, and the like), nitrogen (including one or more nitro groups, nitroso groups, nitriles, amides, imines, amines, zwitterions, betaine groups, and the like), and sulfur (sulfone, sulfonates, sulfonic acids); a monocarboxylic acid and/or their salts selected from acetic acid, propionic acid, benzoic acid, salicylic acid, formic acid, butyric, valeric, caproic, caprylic, capric, lauric, myristic, palmitic, stearic, oleic, linoleic, cyclohexanecarboxylic, phenylacetic, toluic (o, m and/or p), chlorobenzoic (o, m and/or p), bromobenzoic (o, m, and/or p), nitrobenzoic (o, m and/or p), phthalic, isophthalic, terephthalic, p-hydroxybenzoic, anthranilic, aminobenzoic acid (o, m and/or p), methoxybenzoic (o, m and/or p), and the like; and/or dicarboxylic acids and/or their salts selected from succinic acid, malonic acid, oxalic acid, glutaric, adipic, pimelic, suberic, azelaic, sebacic, maleic, fumaric, phthalic, isophthalic, terephthalic, hemimellitic, trimellitic, trimesic, and the combinations thereof; and/or tricarboxylic acids such as citric acid; and/or polycarboxylic acids and/or their salts selected from polyacrylic acid, carboxylate derivatized polysulfonic acid, polymethacrylic acid, copolymers of at least one or more acidic monomers, block copolymers of same; and combinations of two or of the carboxylic acids listed above;

also effective carboxylic acids are one or more of the oxidation resistant members following in any combination and comprising at least one —COOH and/or —COO⁻ group bonded to atoms of C and H as "oxygenated hydrocarbons" of aliphatic or aromatic groups, R, R' and/or R", or a combination of aromatic and aliphatic groups ("alkylaryl"), of carbon number range of 1 to about 40 when present as individual compounds, or with a molecular weight of 200 to about 10,000 Daltons when present as oligomers, or with a molecular weight of 2,000 to about 3,000,000 Daltons when present as polymers (including cross-linked aliphatic and/or aromatic polymers), and which can also contain groups or atoms of non-C and H such as halogens, pseudo halogens, oxygen (including ethers, alcohols, carboxylic acids, ketones, aldehydes, and the like), nitrogen (including one or more nitro groups, nitroso groups, nitriles, amides, imines, amines, zwitterions, betaine groups, and the like), and sulfur (sulfone, sulfonates, sulfonic acids); a monocarboxylic acid and/or their salts selected from acetic acid, propionic acid, benzoic acid, salicylic acid, formic acid, butyric, valeric, caproic, caprylic, capric, lauric, myristic, palmitic, stearic, oleic, linoleic, cyclohexanecarboxylic, phenylacetic, toluic (o, m and/or p), chlorobenzoic (o, m and/or p), bromobenzoic (o, m, and/or p), nitrobenzoic (o, m and/or p), phthalic, isophthalic, terephthalic, p-hydroxybenzoic, anthranilic, aminobenzoic acid (o, m and/or p), methoxybenzoic (o, m and/or p), and the like; and/or dicarboxylic acids and/or their salts selected from succinic acid, malonic acid, oxalic acid, glutaric, adipic, pimelic, suberic, azelaic, sebacic, maleic, fumaric, phthalic, isophthalic, terephthalic, hemimellitic, trimellitic, trimesic, and the combinations thereof; and/or tricarboxylic acids such as citric acid; and/or polycarboxylic acids and/or their salts selected from polyacrylic acid, carboxylate derivatized polysulfonic acid, polymethacrylic acid, copolymers of at least one or more acidic monomers, block copolymers of same; and combinations of two or more carboxylic acids listed above;

and/or sulfonic and other sulfur-based acid selected from methanesulfonic acid, petroleum sulfonates, sulfuric acid, lauryl sulfonic acid, toluenesulfonic acid (o, m and/or p), organosulfonic acid, singular or polysulfonated aromatic compounds, alkylsulfonic acid, arylsulfonic acid, alkylarylsulfonic acid, and combinations thereof;

and/or polysulfonic acid and/or their salts including copolymers, block copolymers, containing hydroxyl groups, or keto groups, and the like as listed above.

and/or acidic inorganic salts such as sodium and potassium salts of hydrogen sulfate, and/or protonated phosphates such as phosphoric acid, orthophosphate (monobasic and dibasic), protonated phosphonates and protonated phosphinics, and/or silica gel, aerogel, fumed silica, diatomaceous earth, and the like, and most preferably pre-washed with an acetic aqueous solution or other acidic material if used as Part B, or with an alkaline wash if used as Part A.

and/or alumina, preferably fine grained alumina, and most preferably alumina pre-washed with an acetic aqueous solution or other acidic material.

and/or bicarbonate ion, $HCO_3^-$, and its salts, and carbonate ion, $CO_3^=$ blended with acidic materials, and its salts, and/or boric acid, borate, and tetraborate (e.g. borax), acidic metal ion salts such as cationic ions of aluminum, zinc, ferric ion, ferrous ion, magnesium ion, lithium ion, titanium (III or IV), gallium, acidic zirconates, stannic ion, rare earth group ion(s); and mineral acids such as $H_nX$ where X="SO4" ion (sulfuric acid or bisulfate ion) (n=2), and phosphoric acid (n=3).

Combinations selected from any of the above acids may also be used.

Although HBr and HI are effective, these acids also result in undesirable oxidation of their anions, i.e. iodide forms triiodide and bromide forms bromine.

Representative Reactions and Amount of Acid Required

Representative chemical reaction examples, using preferred oxidatively resistant acids and/or buffers, are given as follows using potassium ferrate(VI) as the preferred choice of ferrate(VI), and FeOOH as representative of the ferric containing product:

$$2K_2FeO_4 + 4RCOOH \rightarrow H_2O + 4RCOO^-K^+ + 2FeOOH(s) + 3/2 O_2\uparrow(g) \quad (1a)$$

Where carboxylic acid "R" group, R—, can be alkyl, aryl, or alkylaryl and/or where substituents such as halogens, nitriles, other phosphonates, carboxylate, nitro groups, and the like can be included as part of the alkyl or aryl groups such that they do not interfere with the $O_2$ production reaction. Four equivalents of proton donor acid or buffer provides the maximum amount of O2 produced (Reaction 1a). However excess acid drives the formation rate of O2 faster and so may be preferred. However excessive acid or pH buffer is to be avoided since it adds weight which is undesirable for any portable product. The lowest radical weight of the R group also allows the maximum amount of $O_2$ produced per unit weight of formulation and can also increase the rate of $O_2$ production by the associated water solubility of lower carbon number materials and by increasing the hydrogen ion activity in the water. Using acetic acid as an example of an oxidatively resistant monocarboxylic acid:

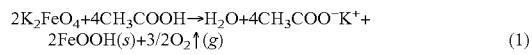

$$2K_2FeO_4 + 4CH_3COOH \rightarrow H_2O + 4CH_3COO^-K^+ + 2FeOOH(s) + 3/2 O_2\uparrow(g) \quad (1)$$

Weak acid ion exchange macroporous and ion exchange resin gels can be used in a similar fashion but these react a little slower than the mono, bis, tris or tetrakis carboxylic acids. These reactions with polymers are exemplified in this application as, $$2K_2FeO_4 + R_{polymer}[COOH]_4 \rightarrow H_2 + \{R_{polymer}[COO^-K^+]_4\} + 2FeOOH(s) + 3/2 O_2\uparrow(g) \quad (1b)$$

Reaction (2) illustrates using hydrated organosulfonic acid as the oxidation resistant and efficient acid to cause fast O2 generation from aqueous blends of ferrate(VI) salts:

$$2K_2FeO_4 + 4RSO_3H = H_2O + 4RSO_3K + 2FeOOH(s) + 3/2 O_2\uparrow \quad (2)$$

Where R— alkyl, aryl, or alkylaryl and/or where substituents such as halogens, nitriles, other phosphonates, carboxylate, nitro groups, and the like can be included as part of the alkyl or aryl groups such that they do not interfere with the $O_2$ production reaction.

Reaction (2) illustrates using organophosphonic acid as the oxidation resistant and efficient acid to cause fast $O_2$ generation from aqueous blends of ferrate(VI) salts:

$$2K_2FeO_4 + 2RPO_3H_2 \rightarrow H_2O + 4RPO_3K_2 + 2FeOOH(s) + 3/2 O_2\uparrow \quad (3a)$$

Where R— alkyl, aryl, or alkylaryl and/or where substituents such as halogens, nitriles, other phosphonates, carboxylate, nitro groups, and the like can be included as part of the alkyl or aryl groups such that they do not interfere with the $O_2$ production reaction. For example, using hydroxyethyldiphosphonic acid (HEDP) or one of its protonated salts as a highly oxidatively stable phosphonic acid with a low equivalent weight, is a most preferred formulation:

$$2K_2FeO_4 + 2CH_3COH(PO_3H_2)_2 \rightarrow H_2O + 2[CH_3COH(PO_3)_2]Fe^{III} + 3/2 O_2\uparrow \quad (3b)$$

Using concentrated or aqueous phosphoric acid is also a preferred acid component of the ferrate(VI)/water mixture:

$$2K_2FeO_4 + 4H_3PO_4 \rightarrow 2K_2HPO_4 + 5H_2O + 2FePO_4(s) + 3/2 O_2\uparrow \quad (4)$$

Phosphates and phosphonates have the additional advantage of buffering the pH near neutrality, from about pH 5 to about pH 10, and especially from about pH 6 to pH 9, and particularly effective in pH buffering the pH to the most neutral pH 7 to 8 region.

Using "solid acid" bisulfate buffer is most preferred acid since its solid form makes the component mixture very easy to handle and store relative to liquids:

$$2K_2FeO_4 + 4NaHSO_4 \rightarrow H_2O + 2K_2SO_4 + 2Na_2SO_4 + 2FeOOH(s) + 3/2 O_2\uparrow \quad (5)$$

Using hydrated silica gel:

$$2K_2FeO_4 + 2Si(OH)_4 \rightarrow H_2O + 4K_2SiO_3 + 2FeOOH(s) + 3/2 O_2\uparrow \quad (6)$$

Using "solid acid" bicarbonate ion buffer:

$$2K_2FeO_4 + 4NaHCO_3 \rightarrow H_2O + 2K_2CO_3 + 2Na_2CO_3 + 2FeOOH(s) + 3/2 O_2\uparrow \quad (7)$$

Ferrate(VI) forms ferric oxide or ferric oxyhydroxide when it reacts which is a rust colored and easily disposed solid. Sometimes the rust color of this product is undesirable. This residual color can be controlled by including pH and ferrate(VI) reactivity control reagents in the formulation. These and the above acidic reagents are also useful to blend with ferrate to control the ferrate(VI) oxidation reaction, preventing potentially high pH values in the reaction product mixture, rendering the ferric product lightly or non colored (e.g. ferric orthophosphate product being almost colorless, while other complexing agents can render colored ferric complexes), rendering the ferric product water soluble and/or as a dispersible particulate, and/or coagulating and/or flocculating the ferric product, as is most preferred in the application.

The rate of $O_2$ generation reaction can be set using control of the pH where the higher the acid/ferrate(VI) ratio the faster is the reaction of ferrate(VI) to form $O_2$ and ferric solid (or solubilized) products. Lowering of the acid/ferrate(VI) ratio lowers the ferrate reaction rate and oxidative aggressiveness. Chloride ion, and other halides and pseudo halogens, and bicarbonate ion, and the like increase the reactivity of ferrate ion causing its oxidation reactions to proceed faster. Such benefits are desirable to provide fast, efficient and complete reactions at conditions of mild pH and temperature.

Ferrate can be mixed with other ingredients as mixtures or solid solutions. One preferred formulation method includes preparation of solid solutions of ferrate(VI) ion by ion substitution of at least a 1% portion, preferably a 10% portion of especially sulfate ion ($SO_4^=$) and/or chromate ion ($CrO_4^=$) to form carrier salt materials of ferrate ion ($FeO_4^=$). These are normally produced by the co-crystallization method. Such inorganic materials, salts and minerals include the following:

potassium sulfate (arcanite), calcium sulfate, magnesium sulfate, sodium sulfate, aluminum sulfate, barite (BaSO4), and zinc sulfate, basic (hydroxide ion containing) forms of the above, and/or chromate(VI) replacement forms, one or a combination of the following minerals,
aluminite, (Al2(SO4)(OH)4*7H2O
Alunogen, (Al2(SO4)3*18H2O
Anhydrite, (CaSO4)
Gypsum, (CaSO4*2H2O)
Bloedite, (Na2Mg(SO4)2*4H2O
Glauberite, (Na2Ca(SO4)2)
Hauyne, ((Na,Ca)$_{4-8}$Al$_6$(SiO$_4$)$_6$(SO$_4$)$_{1-2}$
Kainite, (KMg(SO4)Cl*3H2O
Kieserite, (MgSO4*H2O)
Potassium jarosite, [KFe$_3$(SO$_4$)$_2$(OH)$_6$],
Kuzelite, [Ca$_4$Al$_2$(SO$_4$)(OH)$_{12}$*6H$_2$O],
calcium aluminum chromate hydrate, [Ca$_4$Al$_2$O$_6$(CrO$_4$)*(9-14)H$_2$O]
calcium aluminum sulfate hydrate, [Ca$_4$Al$_2$O$_6$(SO$_4$)*14H$_2$O]
ettringite, [Ca$_6$Al$_2$(SO$_4$)$_3$(OH)$_{12}$*26H$_2$O]

Where with each mineral listed above, the $SO_4^=$ is partially or entirely replaced with $FeO_4^=$ ions which have essentially identical molecular dimensions and identical molecular ion electric charge to sulfate ion and chromate ion, and so readily forms solid state "solutions" with minerals and salts of these ions when they are co-crystallized in the same solution. In the above "solid solution" compositions of matter the carrier salt or mineral contains ferrate(VI) ions to the mole fraction of ferrate/sulfate ion or ferrate/chromate ion, from 1 to 100%, preferably 2-10%. When substitution is 100% the new ferrate (VI) compositions of matter are:

potassium ferrate(VI) (ferrate version of arcanite), calcium ferrate, magnesium ferrate(VI), sodium ferrate(VI), aluminum ferrate, ferrate version of barite (BaFeO4), and zinc ferrate(VI), basic (hydroxide ion containing) forms of the above, and/or chromate(VI) replacement forms, one or a combination of the following minerals,
Ferrate version of aluminite, [Al$_2$(FeO$_4$)(OH)$_4$*7H$_2$O]
Ferrate version of Alunogen, [Al$_2$(FeO$_4$)$_3$*18H$_2$O]
Ferrate version of Anhydrite, [CaFeO$_4$]
Ferrate version of Gypsum, [CaFeO$_4$*2H$_2$O]
Ferrate version of Bloedite, [Na$_2$Mg(FeO$_4$)$_2$*4H$_2$O]
Ferrate version of Glauberite, [Na$_2$Ca(FeO$_4$)$_2$]

Ferrate version of Hauyne, $[(Na,Ca)_{4-8}Al_6(SiO_4)_6(FeO_4)_{1-2}]$

Ferrate version of Kainite, $[KMg(FeO_4)Cl*3H_2O]$

Ferrate version of Kieserite, $[MgFeO_4*H_2O]$

Ferrate version of Potassium jarosite, $[KFe^{III}_3(Fe^{VI}O_4)_2(OH)_6]$,

Ferrate version of Kuzelite, $[Ca_4Al_2(FeO_4)(OH)_{12}*6H_2O]$,

Ferrate version of calcium aluminum chromate hydrate, $[Ca_4Al_2O_6(FeO_4)*(9-14)H_2O]$ Ferrate version of calcium aluminum sulfate hydrate, $[Ca_4Al_2O_6(FeO_4)*14H_2O]$ Ferrate version of ettringite, $[Ca_6Al_2(FeO_4)_3(OH)_{12}*26H_2O]$ Note that the use of solid solutions dilute the ferrate(VI) ion to enable it to be spread more evenly at low levels, helps control the rate of $O_2$ generation and/or prevents spontaneous premature decomposition by the second order reaction of two ferrate ions reacting to produce $O_2$ gas.

Other solid solutions of sulfate with similar ferrate(VI) loadings are also preferred, such as those of sodium ion, lithium ion, potassium ion, or other alkali metal ions or alkaline earth ions. Especially preferred formulated materials are anhydrous potassium sulfate and/or anhydrous calcium sulfate solid solutions of ferrate(VI) ion. As examples, the following is a list of some ferrate(VI) composition mineral-based compositions:

Ferrate(VI) solution of jarosite structure, i.e. $KFe_3(Fe^{VI}O_4)_2(OH)_6]$ as an essentially pure compound or fraction of potassium jarosite material. This new composition also pertains to other jarosites too, such as where $K^+$ is replaced in whole or in part by $Na^+$, $Ag^I$, $NH_4^+$, $Tl^+$, $Li^+$, and the like, where again Roman numeral subscripts refer to formal oxidation states on the metal ion, while +'s and −'s refer to electric charges on the ions.

Ferrate(VI) solution of Kuzelite, $[Ca_4Al_2(Fe^{VI}O_4)(OH)_{12}*6H_2O]$, as an essentially pure compound or fraction of Kuzelite material.

Ferrate(VI) solution of calcium aluminum chromate hydrate, $[Ca_4Al_2O_6(Fe^{VI}O_4)*(9-14)H_2O]$, as an essentially pure compound or fraction of calcium aluminum chromate hydrate material.

Ferrate(VI) solution of calcium aluminum sulfate hydrate, $[Ca_4Al_2O_6(Fe^{VI}O_4)*14H_2O]$. calcium aluminum ferrate hydrate Ferrate(VI) solution of ettringite, $[Ca_6Al_2(Fe^{VI}O_4)_3(OH)_{12}*26 H_2O]$ The above listed materials in completely or substantially dehydrated form.

silicates, clays, oxides, sulfates, and/or phosphates, any combination of those listed above.

The ferrate(VI) compositions of this invention can take many physical forms. Examples include powders, crystals, pastes, gels, granules, pellets, tablets, impregnated pads, lozenges, briquettes, pills, salves, dusts, creams, foams, and combinations of these.

Ferrate(VI) can be combined with materials including binders, compatibilizers, homogenizers, stabilizers (chemical and physical), and/or diluents.

Finished commercial product formulations often contain other ingredients to increase product manufacturability, handleability and cost performance. Other ingredients may also be added that are end-use specific. For example oxidation resistant binders, such as basic clays, kaolin clay, petroleum jelly, paraffin wax, and the like, at the 0.1% to 10% level, preferably at the 1 to 5% level, and most preferably at the 1.5 to 3% level, could be added to ferrate(VI) salts and/or solid solutions to enhance the internal adhesive strength of pellets and briquettes used to charge $O_2$ generation cartridges to minimize dusting that might cause dusting during manufacture, shipping, and handling, or cause entrained particulates to follow the $O_2$ gas as it exits the unit during use as to provide breathing $O_2$ to an ambulance patient during emergency situations or a warfighter in a battlefield situation (although the apparatus will typically be fitted with a particulate filter to prevent any such particulate transfers from reaching the person(s) breathing the $O_2$ produced). Ingredients can be used as binders to control particle size and shape, processing aids to maintain flow during production transfers (flow aids), packaging and use, inert diluents to control $O_2$ generation rate and cost/performance, to provide pH buffering, and the like. Such ingredients can be used in the ferrate(VI) containing Part alone or as multi-part compositions. Designing in multiple such performance features for each ingredient is most preferred to maximize cost benefit per unit weight and per unit bulk volume of $O_2$ generator product; for example per cartridge. Examples of such formulating ingredients (using commercially used ingredient label names as well as some with chemical names) useful in preparing $O_2$ generating materials include: alumina, titania, silicates such as aluminum magnesium silicate (examples of flow aids), silica (example of a desiccant to extend shelf life and increase usefulness in humid environments), aluminum monostearate (example of a pellet mold release), bentonite (example of a silicate clay), benzalkonium chloride, Benzethonium chloride, benzyl benzoate, butyl alcohol, calcium carbonate, calcium phosphate, calcium stearate, calcium sulfate (example of diluent to control $O_2$ release rate and to increase cost performance), vegetable oils (to provide paste characteristics), carbon black (to increase $O_2$ generation rate, for example in welding applications), carboxymethylcellulose, carrageenan, (example of a binder) cellulose and its derivatives, cetostearyl alcohol, hexadecanol, hexadecanoic acid hexadecyl ester, cetyl esters wax, charcoal, cholesterol, cocoa butter, (useful to produce pastes, decrease brittleness of pellets, prepare creams and slurries, etc. without causing dissolution of the ferrate(VI) crystals, etc.), Croscarmellose sodium, Crospovidone (tablet disintegrates), Cyclopolydimethylsiloxane, Diacetylated Monoglycerides, Dibutyl 1,8-octanedicarboxylate, diethyl phthalate, dimethicone, Docusate sodium, Ethylcellulose, gelatin, glycerin, glyceryl Monostearate, glyceryl Palmitostearate, Glycofurol, guar gum, Hydroxyethyl cellulose, Hydroxypropyl cellulose, hydroxypropyl methylcellulose, hydroxypropyl methylcellulose phthalate, Imidurea, isopropyl myristate, isopropyl palmitate, kaolin (a clay), lactitol, lanolin, lecithin, ammonium lauryl sulfate, guar hydroxypropyltrimonium chloride, methyl cellulose, methyl isobutyl ketone, methyl paraben, mineral oil, magnesium aluminum silicate, magnesium carbonate, magnesium oxide, magnesium silicate, stearate, pectin, petroleum jelly, polypropanoic acid (2-hydroxy-homopolymer), poly(methacrylic acid, methyl methacrylate), polydextrose (flow aid), polyethylene glycol monoleyl ether, polyethylene glycol monostearyl ether, polyethylene oxide, polymethacrylates, polyoxyethylene alkyl ethers, polysorbate, polyvinyl alcohol, potassium benzoate, providone, propyl 3,4,5-trihydroxybenzoate, propylene carbonate, propylene glycol, alginates, sodium benzoate, sodium borate, sodium citrate, methane sulfonic acid, (provides a useful pH adjustment downwards to offset the pH rise ferrate can cause in certain cases, e.g. when ferrate(VI) does not have anything else to react with and so reacts with water: i.e. Equation (8). The chemistry of Equation (8) helps to maximize the amount of $O_2$ produced per unit weight of product since pH buffers(s) can be reduced or omitted. Omitting buffers results in a high amount of $O_2$ produced per unit weight of formulation as shown by the following reaction:

$$2K_2FeO_4 + 3H_2O \rightarrow 2FeOOH + O_2\uparrow + 4KOH \qquad (8)$$

The pH will rise during the $O_2$ gas generation by Reaction (8), the $O_2$ generation rate will slow down markedly due to this rise. This slow down is preferred in those cases where slower $O_2$ production rates are desired or when $O_2$ generation is desired to be produced ahead of its time of use and there is less need for speed of production. A mist eliminating inline cartridge can be optionally included with the vessel to prevent a possible caustic aerosol from following the $O_2$ gas from the unit to the application. The presence of KOH also slows down the rate of $O_2$ formation from ferrate(VI) which may or may not be desirable depending on the application (as noted above).

Reagents such as sodium thiosulphate (this reagent will instantly reduce ferrate to ferrous/ferric, and so is an way to quickly discharge ferrate(VI)) could be included an optional kit as "Part D" to destroy any excess ferrate(VI) prior to disposal or contact by first responders.

Ferrate(VI) can be combined with other $O_2$ generating agents, for example with urea peroxide, hydrogen peroxide, perborate, alkyl peroxides, aromatic peroxides, polymeric peroxides, ozone, persulfate, percarbonate, mixtures of these, and the like. Some of these $O_2$ generating agents would be more stable in the presence of ferrate than others. Hydrogen peroxide based formulations would be the least stable in the presence of ferrate(VI) salts since hydrogen peroxide has similar solvent properties to water and would prematurely dissolve Na or K based ferrate(VI) salts which would promote premature $O_2$ production. However, such peroxides could be a part of a second component with ferrate(VI), e.g. Part B, C or D, which would then provide a secondary sources of $O_2$ generation.

As another aspect of the invention, ferrate(VI) would not only generate $O_2$ gas but the formed ferric product enhances the rate of production of $O_2$ from peroxides as well. This feature is especially valuable when the most stable and/or low cost peroxides are used, such as percarbonate, persulfate, perborate, which react too slowly at room temperature or at cool conditions, and hence have too slow of $O_2$ generating rates.

Some other useful formulation ingredients may include, for example, cetearyl alcohol, petrolatum, mineral oil, ceteareth-20, tocopheryl acetate, magnesium ascorbyl phosphate, retinyl palmitate, dimethicone, cyclopentasiloxane, glyceryl dilaurate, lecithin, stearic acid, aluminum starch octenylsuccinate, carbomer, methylparaben, propylparaben, alcohol, DMDM hydantoin, sodium hydroxide, fragrance, cetrimonium chloride, Quaterium-18, potassium chloride, disodium EDTA, TEA-dodecylbenzenesulfonate, ascorbic acid, tocophenyl ethyl ether, methylchloroisothiazolinone, hydrolyzed wheat protein, hydrolyzed soy protein, and methylisothiazolinone, sodium chloride, citric acid, sodium citrate, passiflora incarnata flower extract, anthemis nobilus flower extract, and PEG-60.

For some applications, where fast generation rate of $O_2$ gas is desired and/or a liquid end product is desired, then it is desirable to include a metal ion ligand, or blend of ligands, where "ligand" is a term well known to inorganic chemists and refers to the conventional inorganic chemistry terminology as any ion, atom or molecule that bonds (or "coordinates") to a metal ion, in this case to the ferrate products of use giving ferric or ferrous ions. One or more ligands are preferred in the formulation when it is desirable to prevent the ferric and/or ferrous ions from forming the ferric oxyhydroxide product "rust" colored stain in its use and instead render the ferric ion product either water soluble, an easily dispersible solid, a certain color, and/or easily disposed of. Preferably the ligand is a metal ion complexing ligand, i.e. binding the metal ion at least with one bond, and most preferably a metal ion chelating agent where two or more points from a single molecule bond to the ferric ion product. And it is preferred to incorporate this ligand along with a ferrate treatment during, or preferably after, use. Collectively these compounds are referred to as ligands. Preferred are those ligands that result in solubilization of ferric iron, and most preferred are those ligands that also buffer the pH. Ligands also buffer the free metal ion activities in aqueous solution, aqueous-based foams or emulsions, in thin moist films, and the like. The metal ion complexing ligand can be applied before, during, or after a ferrate treatment. For example, it is best to add oxalic acid after $O_2$ generation but before disposal to solubilize the product mass as water soluble tris(oxalato)ferrate(III) ion. In some embodiments, the chelating agent is present in a ferrate composition. Chelating agents that form coordinate covalent bonds to and chelate $Fe^{III}$ ions are especially preferred. This solubilization of iron by ligands can be especially desirable to prevent rust stains. Alkyl and alkylamino phosphonates, such as HEDP (Dequest 2010®) are most preferred but many other possibilities exist including hydroxamic acids, catecholates, aminocarboxylates such as EDTA, HEDTA, CDTA, NTA, glycine, and the like, mono, di and tricarboxylic acids such as malonic acid, citric acid, succinic acid (least preferred due to the weak metal ion complexing nature of this ion), tartaric acids, gluconic acid, oxalic acid, and the like, compounds, and other oxidation resistant chelating phosphonates, and the like are examples of chelating agents capable of strongly solubilizing ferric ion.

Particularly desirable ligand and pH buffering components in some ferrate compositions are mono, di, tri, tetra, penta, meta, or poly phosphates, phosphonates, and/or phosphinic compounds used singularly or in any combination. Especially preferred is orthophosphate ($PO_4^{3-}$), phosphonate ($HPO_3^=$), and phosphinates ($H_2PO_2^-$), including their acids, salts and esters, including its protonated forms, i.e. monobasic ($H_2PO_4^{3-}$), dibasic $HPO_4^{2-}$ or tribasic forms, as well as phosphoric acid, and/or polyphosphates and phosphate glasses. Phosphates are most preferred because they are already fully oxidized and therefore immune to further oxidation. On the other hand, sterically hindered phosphonates and phosphinics are also effective where such steric hindrance groups are provided by alkyl, alky lauryl, and/or aryl groups; collectively referred to as "R" groups. R groups can be linear and/or branched hydrocarbons of one to 40 carbons total, although normally each R group would contain no more than 18 carbons. An oxidatively resistant phosphonate example is Dequest® 2010 (Clear Tech Product #DQ21) and similar commercial products, including products produced by DOW Chemical Co. Many pH buffers do not bond to metal ions and so are not ligands. Such compounds are still useful in the invention as pH buffers, normally present at least in part in acidic form to neutralize the hydroxide ions formed during the reactions, for example $O_2$ generating reactions, provided by ferrate.

The function of a pH buffer or metal ion ligand are several. These functions will be illustrated using orthophosphate ion to illustrate. Phosphate buffers the pH, resulting in reaction mixtures that can develop strongly acidic, mildly acidic, essentially neutral, mildly basic, or strongly basic reaction mixtures with ferrate. As ferrate's oxidation potential, and therefore reactivity aggressiveness increases with decreasing pH, this use of buffers offers a means to tune the reactivity to the $O_2$ generating job needed, to prevent harsh conditions in the cases where skin contact is involved, to impart selective or mild reactivity, and the like. The reactivity of Ferrate(VI) can also be varied during the course of a reaction by using conditions allowing pH to vary, i.e. drift up or drift down, during the course of the O2 generating oxidation reaction.

Salts can be used to encapsulate, stabilize and buffer the reactive ferrate(VI) ion for storage and reactivity control reasons. For example, potassium or sodium ferrate(VI) solids can be coated with silica, silicate, one or more sulfates, an alkaline alkali metal, zinc, or aluminum phosphate or carbonate salt, for example $K_2SiO_3$, $K_2HPO_4$, $KHCO_3$, $K_3PO_4$, $K_2CO_3$, $K_2SO_4$ and their Na and/or Li counterparts, alkaline phossy glass, borates, boric acid, borax, including mixtures and blends of these. On contact with water, the water soluble phosphate or other salt dissolves away releasing the ferrate and the phosphate or other buffer, complexing agent, and/or precipitant into the reaction mixture with the acidic Part B component, which binds with the ferric ion produced by the action of Ferrate(VI) in producing $O_2$ gas during its field application.

Preferred counter ions for phosphates include K, Na, $NH_4^+$, $H^+$, Mg, Zn, Ca, Li, Al and/or nonoxidizable rare earths, in any combination, including pure compounds, double salts, jarosites and other similar minerals, or as mixtures.

Ferrate(VI) can be formulated with other materials for any of several reasons. For long shelf-life applications, the formulation contains conditions that do not significantly reduce the stability of the ferrate(VI) salt and protects it from environmental effects that can reduce the stability of ferrate, for example moist atmospheric carbon dioxide. This could be a coating, a solid solution such as a alkali sulfate salt, an openable or breakable compartment, an encapsulant, or any combination of these.

If a color change to colorless is more desirable than to brown, buffer or complexant present in a formulation can bind to the ferric iron product preventing a ferric rust color from forming; however, such additives would reduce the total amount of O2 generated per unit weight/volume of ferrate (VI) formulation.

The reactivity of ferrate(VI) is pH dependent, therefore, ferrate compositions may contain strong acid or low pH buffer modifier(s) to control $O_2$ generation rate. Suitable pH buffers include mineral or organic acids with cations selected from hydrogen ion, alkali, alkaline earth, ammonium, zinc, lanthanide, aluminum, ferric ion, copper(II) ion, salts, alone and in combination, of one or more anions of bicarbonate, phosphates, hydroxide ion, silicate, stannate, stannic, citrate ion, acetate, triethanolammonium, methanolammonium, ethanolammonium, other alcohol amine, alkoxy amines, quaternary ammonium ions (e.g. prepared from aryl and/or alkyl groups, for example tetramethylammonium ions, tetraethylammonium ions, trimethyl benzylammonium ions, trimethyl dodecylammonium ion and other such fungicides, cationic phase transfer catalysts, and cationic surfactants, and the like, alone or in combination), zwitterionic ions (such as silicic acid, sulfate, bisulfate, bicarbonate, carbonate, MSA (methane sulfonic acid), nitric, betaines, N-alkylated betaines, and the like, alone or in combination), chloride ion and combinations thereof. Preferably these ions are protonated, and most preferably protonated such that their aqueous solutions, slurries or emulsions are acidic (pH<7) and still more preferentially, strongly acid (pH<3) and with a large acidity capacity (as determined by NaOH titration to pH 8.3).

Preferably, unless insolubility is the method of storage, the pH of ferrate(VI) formulations have a pH>9. pH adjusting agents, if present, are generally present in an amount of up to about 10%, and more preferably from about 0.05% to about 50%, by weight of the formulation, but can rise to over 90%.

Ferrate(VI) compositions can be protected from moisture and/or atmospheric carbon dioxide, and acid gas, a number ways, for example by incorporation into a matrix material such as potassium sulfate or potassium phosphate, di- or tribasic. A suitable matrix material can be selected from matrix materials such as sulfate salts (solid solutions), calcium carbonate, lime, slaked lime, and combinations thereof.

Preferred ferrate(VI) formulation materials and matrices are those that either are oxidation resistant and/or render the ferrate(VI) too insoluble to react during storage with the formulation matrix. A particularly preferred matrix material is a hydrophobic material into which ferrate(VI) salts can be encased or coated, or simply not soluble in, for protection against environmental exposure, especially humid air containing acidic gases, especially carbon dioxide gas. Dried ferrate(VI) solid material is stable in dry air, especially in dry air with little or no $CO_2$ gas present. We found Ferrate(VI) to be unreactive in nonpolar media, such as oils, solvents, waxes, and the like, or in polar compounds and polymers where <10% moisture is present. Thus, examples of especially preferred ingredients include hydrocarbon or silicone greases, perfluorocarbons, polyvinyl alcohol, poly ethers, polyesters, and the like to prepare fluids, waxes, creams, solids, or oils and the like, used alone or in combination.

In some formulations, there may be an added medicine (such as an anesthetic) that can be breathed in along with the oxygen.

Potassium and sodium ferrate(VI) dissolve essentially instantly (for example 10 or fewer seconds) in the water contained by the acidic resin and self mixes due to the $O_2$ gas release. $O_2$ generation rate can be controlled by particle size, mixing rate and intensity, mass ratios, resin porosity, water content and temperature. The maximum solubility of sodium ferrate(VI) ion is about 25% (by mass in water) and the solubility of potassium ferrate(VI) is about 12%, both at room temperature.

Non-polymeric molecular materials are preferred where the fastest $O_2$ release is desirable, as is the case for first responders in ambulance and battlefield applications. In this case an especially preferred acid material is phosphoric acid, which provides three protons for a molecular weight of only 99 g/mole.

One advantage of the use of oxidation resistant acidic polymers is the opportunity to produce a solid state pastes and/or slurry containing devices and gain from the oxidation resistance of such materials, as well as the slower $O_2$ production rate of such materials when reacted with ferrate(VI) salts with water present. The product could be two apparently dry, easily-flowing powders mixed together in a pouch (for example, a "smack pack") that is, or could be, attached to a breathing apparatus. Thus, during use, the packet of the mixture is rapidly mixed by impact or kneading to initiate $O_2$ generation by bringing all the components in intimate contact.

Some, nonlimiting, examples of nonpolymeric oxidation resistant materials include alkyl-, aryl-, and alkylaryl compounds having from 4 to 24 carbon atoms. Organic compounds, such as alkylsulfate esters or alkyl phosphate esters are not desirable if the alkyl group hydrolyses to an alcohol that is easily oxidized. Hence such alkyl groups of easily hydrolysable acid esters should be tertiary alcohols, R3COH, where the "R" groups can be the same or different and the total carbon number (CN#) of the alcohol can range from CN#4 to CN#24. Other suitable materials include fully oxidized inorganics such as phosphates, sulfates, alkylphosphonates, and the like in molecular form, oligomeric, or polymeric form.

The ferrate(VI) powder is a black to purple microcrystalline powder, with or without a rust hue depending on level of purity. Once the reaction is activated, the ferrate(VI) powder turns into ferric oxyhydroxide "rust" and appears orange-brown in color, thus providing a clear indication of the status of its activity. In some embodiments, the ferrate(VI) is stored in a transparent or translucent compartment so that the user can see whether the ferrate(VI) remains in its active purple state or is spent.

The chemistry of ferrate(VI) generation of diatomic oxygen, $O_2$, as oxygen gas, does not require a catalyst to react with the co-reactant due to the capability of ferrate(VI) to react at ambient conditions, including cold temperatures, though the rate of oxygen generation decreases somewhat with cooling. If the selected combination of acidic material(s) and ferrate(VI) material(s) yield a heterogeneous material, it can self mix once the $O_2$ generation reaction is initiated by the contact. If mechanical mixing is provided, then $O_2$ generation is sped up.

Suitable co-reactant acidic materials include organic acids and inorganic acids. Acids in this case are defined as any liquid, solid, or gaseous hydrogen ion donating material in which the pKa is less than about 8, and preferably less than about 7. Such hydrogen ions do not need to be contained in the material if on contact with water hydrogen ions can be generated, even in small amounts. The amount of acidic, hydrogen ion generating material, can be measured by the pH of the mixture at the start, during the $O_2$ generation reaction phase of the reaction, or at the end of the reaction. If any of these pH readings are less than about 8, then the material is acidic enough to produce $O_2$ gas.

Suitable classes of organic acids include carboxylic acids, sulfonic acids, organophosphoric acid esters, organophosphonic acid esters, organophosphinic acid, and/or blends of these alone or with other nonacid materials, such as fillers and binders, or reactive materials such as stabilizers and pH buffers. Suitable classes of inorganic acids include phosphoric, phosphonic, phosphinic, nitric, hydrochloric, hydrobromic, hydroiodic, sulfuric, bisulfate, bicarbonate, phosphoric monobasic, phosphoric dibasic, silicic, acids and the like, and/or blends of these alone or with other nonacid materials, such as fillers and binders, or reactive materials such as stabilizers and pH buffers. Inorganic and organic acids can be mixed. The organic acids can be smaller molecules, polyacids, oligomers, and/or polymers. Preferred acids are those that are polyprotic since these have a high molar content of $H^+$ ions per mole of compound or mixture. Most preferred are those acids that are oxidatively stable. Most preferred acids are phosphoric acids such as orthophosphoric acid, polyphosphoric acid, 1-hydroxy ethyl-1,1-diphosponic acid (known by such trade names as Dequest 2010, or manufactured by DOW Chemical Co., and the like). Ferrate(VI) naturally reacts fast at room temperatures or below and so does not require a catalyst or heat to generate oxygen.

Water activates the ferrate mixture for $O_2$ production by providing a solvent to dissolve the ferrate crystals. The ferrate crystals are not reactive in the solid form although only a small portion of the ferrate crystal content needs to be dissolved at any time to generate $O_2$. Hence water content control is one means of controlling the rate of $O_2$ production by a ferrate mixture. Therefore it is important to provide at least a small amount of water, preferably at least 0.1 to 25% to retain a solid phase but still generate $O_2$, but more water can be added, from 20 to 50% to form a paste or "mud" material which is easily mixed and from which O2 readily escapes as bubbles, or sufficient water can be added to bring the final water weight % up to 99.9% by weight of the original solid, solution, or slurry mixture containing the ferrate(VI) salt. Excess water is not necessary since the $O_2$ formation reaction also generates sufficient water to satisfy the hydration requirements of the ferric oxyhydroxy product (see chemical equations below). Note that the FeOOH species shown in the reaction equations below are given for illustration only since other iron(III) oxides and/or hydroxides are known to those skilled in the art that could also represent the final products of the iron content of ferrate(VI) and that these could be either amorphous, crystalline or both. Mixtures of such iron(III) oxides also may form. These compounds are considered the same for the purposes of this invention and are referred to collectively as ferric oxyhydroxides or ferric oxides, with the former capturing the understanding that the iron(III) product material can be hydrated and that water is formed during the generation of $O_2$ in a stoichiometric amount (see chemical equations below). Other ferric products formed can include materials provided as part of the matrix that form iron compounds or complexes. For example, when phosphoric acid is used as the acid source then ferric phosphate can be part of the final product mixture after $O_2$ production. Ferric phosphonates also can form when the phosphonic acids are used. For the cases of noncomplexing, or weakly complexing acids, then the ferric oxyhydroxides are form. Ferric oxyhydroxides form ferric oxides if they are allowed to age or dry out (dehydrate). All such ferric compounds have minimal to low toxicity and environmental impact, and therefore can be disposed of as nonhazardous wastes. The completeness of the ferrate(VI) to oxygen gas reaction insures that no ferrate(VI) residual is left in the final product, even at very low levels. Hence it is another feature of this invention that the spent product materials are easily disposed of as nonhazardous wastes and do not negatively impact the environment or represent a reaction or toxicity hazard. The nontoxicity of by-products is an important advantage since $O_2$ generators can be used in a wide variety of applications, used in small amounts, and preferably involve disposable cartridges.

Sodium or potassium ferrate(VI) becomes reactive when dissolved in water or is wetted by moisture present or added in a small amount. Hence water can be added alone or with an acid, buffer and/or with other matrix materials such as binders, etc., to initiate the generation of $O_2$ whereupon even more $H_2O$ is produced. For example, phosphoric acid could be added as an aqueous solution of 0.1 to 87%, or a highly porous, cross-linked, sulfonated polystyrene resin in the acid form where such resins are known to hold substantial amounts of water within their porosity, and/or hydrated silica gel slurry containing 1 to 70% water or more, similar mixtures and/or solutions of the acidic and pH buffer materials listed previously, and the like, including mixtures of these. The following chemical equations represent $O_2$ generating reactions using ferrate(VI).

An $O_2$ generator can be deployed with a rebreather device to recirculate the $O_2$ produced for maximum benefit using a pressure differential sensitive month piece to only supply $O_2$ on demand by the user and thereby also extending the useful breathing period of the apparatus.

One composition utilizes ferrate particles having an aspect ratio of at least 8 and up to about 30. "Aspect ratio" has the standard definition for particle characterization and means a fiber-like length that is at least 10 times greater than width or thickness, preferably a needle-like morphology with a length at least 10 times that of both width and thickness. The composition can be pure ferrate, for example potassium ferrate (VI), sodium ferrate(VI), barium ferrate(VI), lithium ferrate (VI), their hydrates, a mixture of high volume or weight percent ferrate particles and other particles, either intended or byproducts, or ferrate particles dispersed in a matrix comprising any of the materials discussed herein used alone or in any combination.

Binder materials are useful to hold formulated solid products in the shape of objects that are easily used by the consumer, for example tablets, lozenges, granules, sheets or films, pellets, pills, and the like. Oxidation resistant binders are preferred for constructing and holding ferrate(VI) formulations into such objects, such as chopped and micro fibers of fiberglass, wollastonite, tobomorite, talc, mica, diatomaceous earth, milled fiberglass, calcite, chalk, lime, titania, magnesia, slaked lime, and combinations thereof.

A ferrate composition suitable for preparation of $O_2$ gas can include any of the materials described herein as desirable, but preferably comprises a powder, preferably granules, but can also be pellets or tablets. The water content of the formulation can also be contained with the ferrate and acid, and be introduced at moderate excess over the stoichiometric equivalent ratio (see above). The water can be added as a mixture or homogenous blend of $H_2O$ contained in other materials (e.g. as water, humidity, entrained moisture, and/or steam). Soluble or partially soluble ferrate salt crystals (agglomerated or compacted into pellets or granules, etc.) can be combined with an inert or co-reactant binder phase (e.g. a clay, potassium sulfate, a phosphate salt, and the like, alone or in any combination), and/or formed into a solid, a slurry, and/or a solution with pH buffer(s). These ingredients can be kept separate from each other in the solid by using separate grains, encapsulation technology already known in the formulations industry products manufacturers and formulators, or in separate compartments, or a combination of these.

For example a ferrate powder would be combined with oxidation resistant, essentially reducing agent free, binder material such that at least 0.1% ferrate(VI) by weight is dispersed in the formulation, preferably at least 1-10%, and more preferably 10-50%, and most preferably 50-100%. The ingredients can be added together with mixing. The mixture can be mechanically blended by a mixer, sonication, shaking, and any combination of these. Moderate shear conditions, for example using a ribbon mill, can be used to generate a blend which then forms granules naturally, or rolled in a prilling mill, or extruded through a pelletizer, to prepare uniform pellets, pills, tablets, rods, and briquettes (in this invention, any of these forms may be generically called "pellets"). Forming the buffer as separate pellets from the ferrate pellets is also effective, though they can also be combined. Pellets of differing compositions can be co-mixed in a rolling drum mixer in the absence of water to thoroughly intermix the components reactants. These mixtures can be packaged, bagged, stored, and shipped in bulk.

To charge an $O_2$ dispenser, the above ingredients, either immediately upon production, at a later date, and/or at a different location, can be filled into containers designed to handle $O_2$ gas upon the addition of water to the assembled ingredients with or/without mechanical mixing.

During use, a means for mechanical mixing during $O_2$ generation is preferred but not necessary as the $O_2$ gas that is produced self-mixes the medium. It is important that the water and ferrate(VI) salt are not brought together until $O_2$ generation is desired. Tap water or natural surface water, urine, etc. is sufficient to provide the water needed to initiate $O_2$ production. Water that is not contaminated with a reducing agent is most preferred. Note that the $O_2$ can be produced before use provided a vessel of sufficient strength to hold the expected amount of the non-condensable gas until use, at which time the gas is released via a regulator.

Once such materials are wetted or mixed with water from a container or nearby tank or other reservoir, the ferrate(VI) dissolves, along with any acidic or proton donating buffer (which may be redissolved in the buffer), and then $O_2$ generation spontaneously commences. The $H_2O$ must be in liquid, vapor, gas, steam, melting ice, and/or in moist form for the reaction to commence.

The invention also provides a dispenser that comprises a first compartment ("Part A") that contains a ferrate(VI) composition and a second compartment that comprises a material that, when combined with the ferrate composition, activates the ferrate. For example, the first compartment ("Part A") could contain ferrate salt, alone or in a matrix or solid solution or solid mixture, and in the physical form of a powder, granule, rod, and/or pellet form, optionally in a supporting matrix such as a porous dust control bag, a screen-walled liner, etc. The second compartment ("Part B") could contain a water solution of acid or proton-generating buffer. To save weight in hauling, the water could be added to the acid/buffer prior to use ("Part C"). Optionally, the second, the third, or a fourth ("Part D") compartment could contain a pH modifier, catalyst, additional agent of medicinal value, or any component that improves the action of the ferrate in producing $O_2$. The various compartments could be controlled using a digital device and does not necessarily require the user to perform the separate tasks in mixing the components, although they could be mixed manually too. A two or more part design is preferred in that it offers the advantage of maintaining separate compartments for storage in that the ferrate and/or second component could be stable when separate but react when combined. Bicomponent devices are well-known, for example in epoxy glues for home use and soda/acid fire extinguishers, and the like. There are numerous examples of bicomponent dispensers, some recent examples are shown in U.S. Pat. Nos. 6,773,414, 6,708,847, 6,672,483, and 6,520,377, which are all incorporated herein by reference. Preferably, the dispenser could be operated by pressing a single button, single plunger, the end of a flexible tube that would simultaneously dispense the two components into a third compartment that is adapted to be connected to a respirator, preferably with optional service extender technologies such as an "on demand" regulated mouth piece and most preferably of rebreather design. Rebreathers pass the exhaled air through a CO2 sorption device consisting of CO2 sorbents such as soda lime or lithium hydroxide filled cartridges. The components could be sequentially dispensed from a single dispenser, for example as peroxide catalyst is combined with polyester resin to initiate polymerization. One component could be added to the other, this addition could be done batch-wise or at a controlled rate or with a controlled continuous or periodic mixing rate. The two components can be also mixed inside a nozzle, or inside an attached container. The two (or more) parts could also be combined by breaking or dissolving capsules in a composition containing capsules of a first part and a powder, gel or any other form of a second part.

Respiratory apparatus is apparatus used to assist breathing and contains a mask or insert that provides an interface between the oxygen source and the subject to be treated. The respirator typically includes a mask with a headstrap and nose and/or mouth piece. Oxygen could be delivered to a person by a mouth insert (such as at one end of snorkel), a nose insert, or a mask that is adapted to fit over both the nose and mouth. The respiratory apparatus may also include a filter and/or a secondary container for a medicine (such as an antibiotic). Examples of respiratory apparatus, which could be adapted for use (either in part or in whole) with the inventive system include U.S. Pat. Nos. 7,178,524, 7,171,964; 6,510,850; 6,340,024; 6,267,114; and 5,658,221 all of which are incorporated herein as if reproduced in full below. Most preferred are on demand, optionally with a rebreather.

Figure 2:
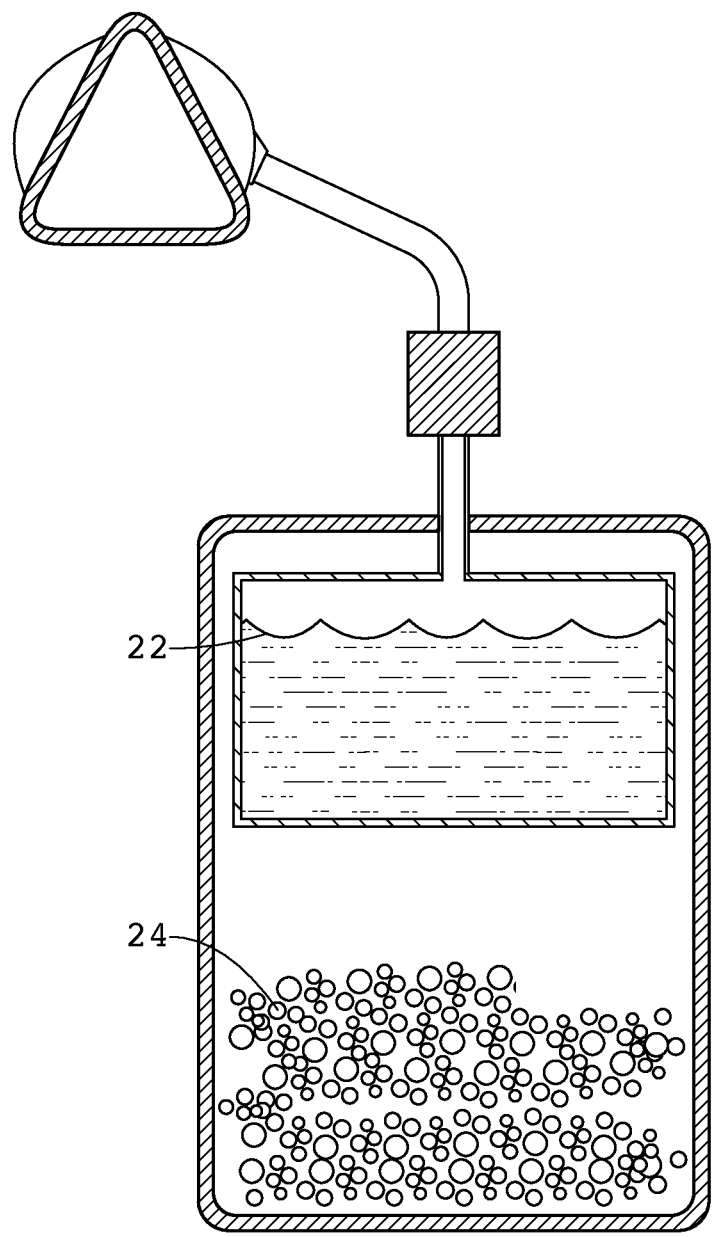
FIG. 2 is a simplified schematic drawing of breathing apparatus.

Views of simple apparatus according to the present invention are shown in FIGS. 1 and 2. A crushable package 10 comprises a first compartment 12 and a second compartment 14. In FIG. 2, a liquid acid 22 is shown in the second compartment 14 and a ferrate composition 24 is shown in the first compartment 12. Of course, these could also be reversed. A breakable wall 16 separates the first and second compartment. The wall 16 is broken to mix the materials in the first and second compartments and start the oxygen generating reaction. In some preferred embodiments, the compositions combine to form a gel. In another embodiment, neither of the compositions are liquids. Oxygen generated by the reaction passes through optional filter element 18. Preferably, the filter element removes aerosols or other particulates. In some preferred embodiments, filter element 18 comprises a nonwettable material, in some embodiments a microporous hydrophobic material. A tube 19 connects the package to respiratory apparatus 20 which in this case comprises a face mask or nasal mask. A flexible seal 21 and an optional strap (not shown) help keep the mask on a patient. An optional pressure sensitive valve 23 can be used to open the flow of oxygen only when the patient inhales. The respiratory apparatus 20 may also include rebreathing apparatus as is known in the art.

Storing ferrate in a sealed container can be hazardous if moisture or humid carbon dioxide gets into the container forming aqueous carbonic acid. Dry $CO_2$ is not a problem, as is low humidity or $CO_2$-free air. Then oxygen gas can be released and a dangerous pressure of $O_2$ gas build-up may occur. Therefore, it is desirable for a container that contains a ferrate composition to have a pressure release valve, and/or be prepared from $O_2$ permeable materials, or constructed strong enough to contain the total $O_2$ gas pressure that could be generated as calculated from the above $O_2$ generating equations. Containers with pressure release valves are known in the art. One example can be seen in U.S. Pat. No. 4,690,667. $O_2$ permeable plastics are known to the food and medical industry.

Ferrate(VI) can react within seconds or extended times (such slower reactions are achieved by reaction with a polymeric acid or by slow addition of ferrate to water or slow addition of an aqueous solution to a ferrate composition). In this manner, reaction times of over 30 minutes or more can be achieved, thereby providing a slower, more controlled generation of $O_2$ gas. The spent ferrate(VI) solution can be discarded simply by pouring into a drain, non-hazardous trash receptacle, slurried down a sink with tap water, a surface water stream, ditch, river, lake, etc. or onto the ground, sand, and the like, or other such readily available location, harmlessly.

EXAMPLES

Testing was performed to evaluate the use of potassium ferrate(VI) as a source of emergency breathing oxygen gas. The results indicate that this invention is generally useful with acids; however, we discovered that particular acids have unexpectedly superior results—these are phosphoric acid, polymeric acids, and carboxylic acids that do not have an α hydrogen. The nonoxidizable mineral acid, phosphoric acid, in both 100% and 10% molar excess, quickly produced the largest amount of oxygen per unit of potassium ferrate(VI), and hence is most preferred, while methanesulfonic acid, dimethylmalonic acid and acetic acid also liberated significant quantities of $O_2$ gas and so are more preferred. However, citric acid is functional but not preferred as it appears is also readily oxidized by the ferrate(VI) and so only produces a low yield of oxygen. Any organic compounds more prone to chemical oxidation than is citric acid and are water soluble would therefore be ineffective in practicing the invention.

Regarding polymeric acids, poly(acrylic acid) also generated oxygen in large amounts when reacting with ferrate(VI) and its viscosity enabled the generation of this $O_2$ gas to occur over a much longer time than did phosphoric acid, and it was also affected most by mechanical mixing intensity. Hence polymeric acids are preferred, and most preferred where slow O2 gas release is needed. Still more preferred are polymeric acids, such as polyolefinic acids with low equivalent weights, such as poly(acrylic acid) and the like. Mixing is useful to control $O_2$ generation rate.

Background

The reaction is the following:

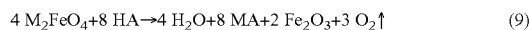

where HA is a weak or strong acid and $A^-$ is the conjugate base and MA its salt with a metal ion, M+. Normally M is K+ or Na+, but can be any metal ions from the list: alkali, alkaline earths, rare earths, zinc, gallium, aluminum, Sc, Y and ferric ion. For the polyvalent metal ions, Equation 9 would need to be adjusted to maintain charge balance.

Phosphoric acid was used to determine if ferrate(VI) oxidation dissolved in water can rapidly produce $O_2$ gas. The chemistry used for this concept evaluation test is believed to be the reaction between ferrate(VI) ion ($FeO_4^{2-}$) and 50% phosphoric acid. The acidity is used to raise the oxidation potential of ferrate(VI) to a high value (>1). Its greatest value, 2.2 V, is reached in strongly acidic solutions. In this manner, ferrate(VI) is strong enough to oxidize the oxide ion ($O^{2-}$), whether from $H_2O$ or from the $FeO_4^=$ ligands, to $O_2$ gas. The balanced chemical reaction is Equation 10:

Experimental Setup

A double-vacuum manifold (a Schlenk Line) with appropriate vacuum fittings/adapters was used to carry out the reactions under vacuum conditions by employing a vacuum pump. An adapter containing a medium pore size frit was placed between the sample flask and the manifold to protect the manifold from any foaming that may occur during the reactions.

A spectrophotometer was used for potassium ferrate assay as well as qualitative permanganate detection. The Perkin Elmer AAnalyst 400 atomic absorption spectrometer (Perkin Elmer, Inc.) was used for quantitative analysis of manganese. GC-MS analysis was performed using an Agilent 6890N Network GC System with 5973 Mass Selective Detector, 7683 Series Injector, and RTX-1701 column (Agilent Technologies, Inc).

Solutions were prepared using ACS grade reagents as well as 18.2 MΩ·cm resistivity high-purity deionized (HPDI) water (Milli-Q, Waters, Inc.). Potassium ferrate(VI) was prepared at Battelle Memorial Institute (Columbus, Ohio, USA), assayed for purity prior to use, and stored under Argon between uses. Eppendorf auto-pipettes and analytical balances were used for 0.1 mg resolution when preparing reagents. High-purity nitrogen (oxygen-free) was used to purge lines and pressurize the manifold when necessary.

Testing was conducted by pouring acid solution onto ferrate in an oxygen-free atmosphere at room temperature (between 19 and 22° C.). The acid solution was degassed by three freeze-thaw cycles prior to use. If needed, the combined ferrate-acid solution was stirred. The presence of $O_2$ was detected using a Clark Cell.

UV-Visible spectroscopy was employed in order to determine the purity of the potassium Ferrate(VI) used throughout the testing. Three potassium Ferrate(VI) solutions were prepared and the Ferrate(VI)($FeO_4^{2-}$) concentration was calculated for each using the Beer-Lambert Law ($A_\lambda = \epsilon_\lambda$ b c). The experimental absorbance values were compared to the theoretical absorbance values at each wavelength. The purity was determined to be 84.94% (by mass).

EXAMPLE 1

Preliminary Evaluation of Acids

Preliminary tests were carried out using each of 3 types of acids: mineral acids, carboxylic acids, and polymeric acids. A 100% molar excess of each acid was added to a measured amount of potassium ferrate in a vial. The reaction was observed for qualitative results only and the pH values were measured.

For the mineral acid, phosphoric acid was used. The reaction was very fast and produced viscous purple/pink slurry with black particles. Vigorous bubbling was seen.

Two carboxylic acids were tested. Acetic acid reacted very quickly with the potassium ferrate and produced a dark red/brown liquid with pH of around 4. The acetic acid odor were very prominent.

A less volatile carboxylic acid, citric acid, was tested. The rate of reaction was slower than that of acetic and phosphoric acids and produced an orange liquid with a pH of about 3. In both cases, vigorous bubbling was noticed.

The reaction of poly(acrylic acid) with potassium ferrate was very slow but steady. The rate of reaction was most likely controlled by the viscous nature of the acid itself. The product was a thick mixture of dark red/brown liquid and dark clumps. The strong color did not allow an accurate pH measurement. Bubbling was noted but at a much slower rate than that observed using other acids.

EXAMPLE 2

Phosphoric Acid/Potassium Ferrate Evaluation: Blank Run

For the following quantitative tests, an excess of the acid was used so that the limiting factor in the reaction was the amount of ferrate(VI) present rather than the amount of acid. Initially, a 100% excess was used, but in further tests was reduced to 10% to determine if the same results could be obtained from a smaller amount of acid.

The test procedure was performed in the absence of the potassium ferrate in order to determine if the gas generated was a product of the acid itself. In this experiment, no gas was generated, proving that the actual acid/ferrate reaction was the source of the gas and oxygen.

EXAMPLE 3

Phosphoric Acid/Potassium Ferrate(VI) Evaluation: 100% Excess $H_3PO_4$

Three trials of the reaction using phosphoric acid in 100% excess were performed. Results of trial one deviated greatly from the next two. It is believed that a small leak may have been created in the system during Trial 1 causing an unusually high pressure increase so its results were not considered in the conclusion. Trials 2 and 3 were much more alike and resulted in an average of 0.786 moles of gas generated per mole of potassium ferrate. This value is close to the theoretical yield of 0.750 moles of oxygen per mole of potassium ferrate. In each case, a significant increase in output of the oxygen-selective Clark Cell proved that the gas created was, in fact, oxygen. Results are shown in Table 1.

TABLE 1

Results of Reaction of 100% Excess $H_3PO_4$ with Potassium Ferrate(VI)

| Trial | Vol. of Acid (mL) | Mass of $K_2FeO_4$ (g) | Amount of $K_2FeO_4$ (mmol) | Vol. of Acid per Gram of $K_2FeO_4$ (mL/g) | Reaction Time (min) | Reaction Temp (° C.) | Pressure Increase (Torr) | Amt. of Gas Generated (mmol) | Amt. of Gas Generated per mole $K_2FeO_4$ (mol/mol) | Oxygen Detected by Clark Cell? | pH of product |
|---|---|---|---|---|---|---|---|---|---|---|---|
| 1 | 1.025 | 0.2735 | 1.381 | 3.75 | 50 | 21.3 | 80.0 | 1.81 | 1.31 | yes | 3 |
| 2 | 0.922 | 0.2458 | 1.241 | 3.75 | 40 | 19.7 | 44.0 | 1.00 | 0.806 | yes | 3 |
| 3 | 0.858 | 0.2289 | 1.156 | 3.75 | 42 | 20.2 | 39.0 | 0.885 | 0.766 | yes | 3 |

The slightly exothermic ferrate/phosphoric acid reaction produced significant bubbling immediately, and slowed as the reaction proceeded. Self-mixing caused by the production of the gas was observed to have occurred. More mixing appeared would be beneficial to thoroughly blend the two reagents so a magnetic stir bar was used to push the reaction to completion.

The final product was a purple/pink paste with dark clumps and a pH of approximately 3. This pH is consistent with the large excess of acid used and indicates the natural buffering system of phosphoric acid couple $H_3PO_4/H_2PO_4^-$. The strong purplish-pink color of the product was consistent with a very small amount of permanganate compound known to be an impurity in some potassium ferrate preparations. To confirm that the residual color was that of permanganate and not ferrate, a qualitative analysis by UV-Visible spectroscopy was performed on the product. The spectrum in the range of 450-600 nm showed 5 peaks consistent with those of a permanganate standard. The permanganate was an impurity in the potassium ferrate as a result of manganese impurities in the iron anodes used during the electrochemical synthesis of the potassium ferrate. The amount of manganese was quantified by atomic absorption spectroscopy. Results showed that manganese was present at 1.8 micrograms per milligram of potassium ferrate. It is known that $O_2$ is not generated on acidification of permanganate solutions. In other work, permanganate-free ferrate was produced using manganese-free iron anodes during ferrate production, and these preparations did not produce the pink end product color when acidified.

EXAMPLE 4

Phosphoric Acid/Potassium Ferrate(VI) Evaluation: 10% Excess $H_3PO_4$

Replicates of this test were performed with 10% excess acid (1.13 mL acid reacted with 0.2355 g $K_2FeO_4$) and unexpectedly yielded higher amounts of gas produced than those of the 100% excess tests. The reactions were conducted at 20.2° C. for 14 minutes and 20.6° C. for 10 minutes yielding 0.874 and 0.851 mol of gas were produced per mole of potassium ferrate used, respectively. An average of 0.862 mol of gas were produced per mole of potassium ferrate used. The Clark Cell showed significant increase in output consistent with the presence of oxygen.

This reaction was also slightly exothermic and also produced vigorous bubbling initially, which decreased as the reaction went on. However, the reaction rate was unexpectedly much higher than was seen in the 100% excess tests. Self-mixing was still not sufficient to carry out the reaction to completion and, therefore, stirring was provided by using a magnetic stir bar.

The final product of these reactions was very similar in texture and color to that of the 100% excess tests except that it did not contain the dark clumps seen earlier. This may be due to the higher water content of the acid solution used. Even though a much smaller amount of acid was necessary in these reactions, the volume of acid solution used was slightly higher than that of the 100% excess tests in order to better facilitate mixing. This was done by decreasing the concentration of the acid solution, thereby increasing the water concentration.

The pH of the product was in the range of 6 to 7 which showed that the decrease in the amount of acid used created a much more neutral product. This pH corresponds to the $H_2PO_4^-/HPO_4^{-2}$ buffer system, a mixture regarded as harmless.

EXAMPLE 5

Figure 3:
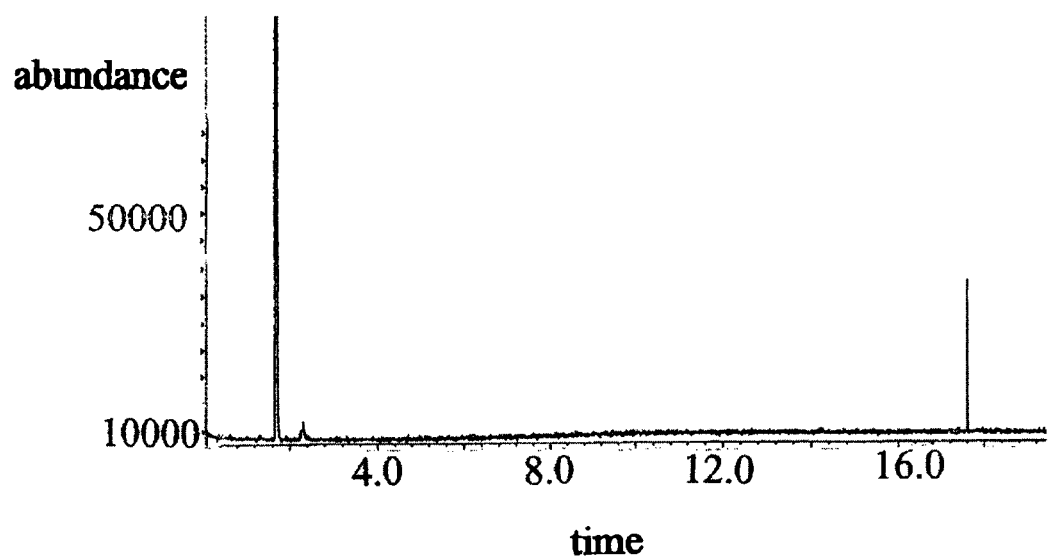
FIG. 3 is a gas chromatogram of product gas from the reaction of potassium ferrate with 10% excess $H_3PO_4$.

Phosphoric Acid/Potassium Ferrate Evaluation: Qualitative Search for Formation of Other Volatile Contaminants The system was pressurized to 750 Torr with nitrogen and the gas product was sampled (100 μL) in gas-tight Hamilton syringes and analyzed by gas chromatography-electron impact ionization mass spectrometry (GC-MS) in full scan mode in order to determine what, if any, volatile contaminants are produced by the reaction. FIG. 3 shows a gas-chromatogram of the product gas. Mass spectral interpretation revealed that the two peaks on the ends represent a mixture of nitrogen (28 m/z), oxygen (32 m/z), and a very small amount of argon (40 m/z). The small peak in the middle is residual water (36 m/z). Based on these results, it appears that this reaction does not produce any harmful volatile chemicals that might be objectionable to breathing with the O2 gas produced.

EXAMPLE 6

Acetic Acid/Potassium Ferrate Evaluation

Acetic acid was evaluated in the same manner as phosphoric acid, at room temperature, and with a reaction time of 2 min. A single test using a 100% excess of acid resulted in a good yield of 0.688 mol of gas per mole of potassium ferrate used. This is close but lower than the theoretical yield of 0.750 mol of oxygen per mole of potassium ferrate and lower than that seen in the phosphoric acid testing. Clark Cell output confirmed the presence of oxygen.

The reaction using acetic acid progressed very rapidly, with about 95% of the gas being produced in the first 10 seconds. Self-mixing was, in this case, was observed to be sufficient and no external mixing source was used, indicating further usefulness of carboxylic acids. The final product was a dark red, non-viscous liquid with a strong odor of acetic acid. For breathing purposes, it is likely that this acetic acid vapor would need to be substantially removed, for example, by an in-line activated carbon sorbent or soda lime sorbent cartridge, the latter is already used in cleaning breathing gases of the acid gas carbon dioxide.

EXAMPLE 7

Citric Acid/Potassium Ferrate Evaluation

Results of duplicate tests using citric acid were conducted. A 100% excess of citric acid resulted in a yield of 0.378 mol of gas per mole of potassium ferrate(VI). Although a amount of gas was generated by the reaction, little or no increase in Clark Cell output was observed. Thus, little or no oxygen was produced.

The rate of reaction was only slightly slower than that of acetic acid, but also produced the majority of gas during the initial 10 seconds of the reaction. No outside mechanical mixing method was needed as self-mixing caused by the off gassing was sufficient. The product was an orange/brown non-viscous liquid, which changed over time to a greenish yellow color. pH was approximately 3. Given these data, the released gas was not oxygen but most likely was $CO_2$.

EXAMPLE 8

Methanesulfonic Acid/Potassium Ferrate Evaluation

To evaluate a broader range of acid structures, the mixed organo-inorganic compound, methanesulfonic acid (MSA), was evaluated using the same conditions as the other examples with a 2 min reaction time at 20.6° C. A 100% excess of acid (1.748 mL acid to 0.1499 g $K_2FeO_4$) resulted in a yield of 0.647 mol of gas per mole of potassium ferrate. Clark Cell output confirmed the presence of oxygen. This is a lower yield than that produced by phosphoric acid but is still good and similar to that of acetic acid. The rate of reaction was also very similar to that of acetic acid. It produced a brown, non-viscous liquid with a pH of 1-2. Self-mixing was sufficient.

The gas produced by this reaction was sampled in gas-tight syringes and analyzed by GC-MS in full scan mode in order to determine volatile contaminants are produced by the reaction. As was the case before, the peaks at approximately 1.7 and 13.5 minutes were attributed to oxygen, nitrogen, and a small amount of argon while the peak at 2.5 minutes is residual water. However, a peak at approximately 4.5 minutes showed the presence of acetone. This acetone most likely did not originate with the MSA and instead originated from the acetone-rich environment surrounding the system due to the dry ice/acetone trap, which can be attributed to the acetone/dry ice bath rather than being a contaminant of the product gas. Acetone is known to coat glass surfaces and can cross contaminate during cleaning and air flushing of the vacuum line during handling whereupon it remains sorbed onto glass surface even while the components of the air is thoroughly removed. Based on these results, MSA can be used for oxygen production from ferrate. The good equivalent weight, ease in handling, and low industrial cost of MSA also makes it an especially preferred acid.

EXAMPLE 10

Dimethylmalonic Acid/Potassium Ferrate Evaluation

The carboxylic acids tested to this point had undesired results in the possible oxidation of citric acid and the volatility of acetic acid. Due to this, a non-volatile carboxylic acid, dimethylmalonic acid (DMMA), was chosen in the hope that the lack of alpha-hydrogens would prevent the oxidation of the carbonyl group. Results were very good, yielding 0.701 moles of gas per mole of potassium ferrate(VI) when using 100% excess of acid. Clark Cell output confirmed the presence of oxygen.

The reaction proceeded very fast and the off gassing of the oxygen was sufficient to mix the reagents thoroughly. The product was an orange/brown non-viscous liquid with a pH of about 3 to 4. Based on these results, DMMA appears to be a suitable oxygen-generating totally organic and non volatile, low odor, low equivalent weight, co-reagent with ferrate(VI).

Discussion of Results

It was discovered that the ferrate(VI) oxidation of oxide ions and/or water to $O_2$ gas can be made to occur quickly and controllably, and that the oxygen produced is in high purity, suitable for and fast enough for point of use needs such as breathing, especially emergency breathing (ambulatory, battlefield wounded, and the like), purposes, field repair welding, chemical synthesis, coal mine (and other mining), rescue, chemically pressurizing $O_2$ (without the need for mechanical pressurization), individual breathing apparatus for submarines, scuba diving, fire fighting, and the like, while forming readily disposable, innocuous byproducts such as mild pH rust slurry.

It was shown that by using phosphoric acid, acetic acid, methanesulfonic acid, and/or dimethylmalonic acid, that oxidatively resistant weak acids, inorganic, organic or mixed organic/inorganic, in general are capable of increasing the oxidation potential of ferrate enough to facilitate $O_2$ production.

Phosphoric acid, a nonvolatile mineral acid, worked well creating suitable conditions for this reaction to take place. It yielded the largest amount of oxygen of all the acids tested. Also, because of its low equivalent weight it required the smallest amount of acid to carry out the reaction, which would lead to a more efficient breathing oxygen generation system. A 10% excess of phosphoric acid was shown to be sufficient and actually, and unexpectedly, produced a superior reaction, perhaps due to its neutral pH. GC-MS analysis showed no unwanted byproducts in the product gas. Hence oxidatively stable, non-volatile, acids, especially mineral acids, are preferred to practice this invention. This classification includes sulfuric acid, solid acid (sodium bisulfate), polyphosphoric acids, and the like. Nitric and hydrochloric acids are less preferred since these acids are slightly volatile from water solutions and therefore would require that the $O_2$ gas product be cleaned of such acids using a pH basic sorbent such as soda lime, lime, slaked lime, lithium carbonate, lithium hydroxide, caustic soda (NaOH) pellets, KOH, and the like. Carbonates are not preferred for this role since they would add $CO_2$ gas to the $O_2$ gas product, rendering it unsuitable for breathing, although the $CO_2$ may not be objectionable for other applications such as in welding, and plant growth stimulation.

Dimethylmalonic, methanesulfonic, and acetic acids also produced considerable amounts of oxygen, although acetic acid would require VOC control; for example using soda lime sorbent beds, for the breathing application due to its high volatility to remove traces of the acid in the oxygen generated.

The rate of $O_2$ production was found to depend on the ability of the two reagents to mix thoroughly, which itself depends on the viscosity and volume of acid solution used. The extremely viscous polymeric acid reacted very slowly, especially when compared to reactions using much less viscous acids like acetic acid and DMMA. However, this viscosity could be adjusted thermally and by increasing moisture content, and so is a tunable property to control $O_2$ production rate. Also, those reactions which required larger volumes of acid solution proceeded more rapidly and were more capable of self-mixing. For example, citric acid which required ~10 mL of acid solution per gram of potassium ferrate was able to self-mix to achieve complete reaction, while 10% excess phosphoric acid which required ~5 mL of acid solution per gram of potassium ferrate benefited from mechanical mixing assistance. We note that it is desirable that the total weight of an apparatus is minimized for size, weight and cost considerations. Hence, since the oxide ion is sufficient for the $O_2$ generation, and water is mostly just the solvent (Reaction 1a), that the water content be minimized for the needs of each application. Presence of some water is preferred to facilitate the reaction of ferrate(VI) ion by dissolving its source crystal. Also, in some preferred embodiments, 0 to 30%, more preferably 0 to 20% of excess acid is used in the reaction to generate oxygen, and this amount of excess surprisingly results in greater oxygen production than the use of greater amounts of acid.

One problem encountered during testing of the carboxylic acids was the apparent oxidation of the acid resulting in diminished oxygen production. This was very evident in the citric acid testing, which produced little or no oxygen. In order to avoid this phenomenon, a carboxylic acid with no alpha-hydrogens was tested. Dimethylmalonic acid has two methyl groups attached to the alpha-carbon of the carbonyl instead of hydrogens. These methyl groups prevent formation of oxidized intermediates that would otherwise occur with α-hydrogen such as H-abstraction, α-elimination, carbanion formation, hydroxyl abstraction, and the like. This helps stabilize the carboxylate and prevent oxidation allowing the ferrate to react with the water or oxoanion oxide ions rather than the acid, while the acid only provides a $H^+$ ion source and pH buffer. Hence, easily oxidized organic or inorganic or mixed organic/inorganic acids, or conditions that make certain acids easily oxidized (e.g. temperatures above 50° C.) are not preferred for the invention.

The invention claimed is:

1. An oxygen dispenser, comprising:
   a first compartment comprising ferrate(VI);
   a second compartment comprising water in the presence of an acid, wherein the amount of the acid in the second compartment in comparison to the amount of the ferrate (VI) in the first compartment is such that there is a stoichiometric molar excess amount of acid in a range of 0 to 100%; and
   a respiratory apparatus; wherein when in use, the ferrate (VI) in the first compartment is combined with the water and acid in the second compartment to generate oxygen for breathing applications, resulting in an aqueous composition having a pH in the range of pH 1 to pH 8.

2. The dispenser of claim 1, wherein the respiratory apparatus comprises a mask adapted to be worn on the face of a person.

3. The dispenser of claim 1 or 2, wherein the respiratory apparatus comprises a nasal mask.

4. The dispenser of claim 1, wherein the first and second compartments are separated by a breakable wall.

5. The dispenser of claim 1, wherein the amount of the acid in the second compartment in comparison to the amount of the ferrate(VI) in the first compartment is such that there is a stoichiometric molar excess amount of acid in a range of 0 to 50%.

6. The dispenser of claim 1, wherein the acid comprises a carboxylic acid that does not have an alpha hydrogen, a phosphoric acid, a polymeric acid, a sulfonic acid, a sulfuric acid, a ferric ion salt, an aluminum ion salt, a zinc ion salt, a silicic acid, a phosphonic acid, or a blend or mixture of thereof.

7. The dispenser of claim 1, wherein the acid comprises a solid acid ion exchange resin.

* * * * *